US012378268B2

(12) United States Patent
Yu et al.

(10) Patent No.: US 12,378,268 B2
(45) Date of Patent: Aug. 5, 2025

(54) HETEROCYCLIC THR-β RECEPTOR AGONIST COMPOUND AND PREPARATION METHOD AND USE THEREFOR

(71) Applicant: Hepagene Therapeutics (HK) Limited, Hong Kong (CN)

(72) Inventors: Shanghai Yu, Suzhou (CN); Ben Li, Suzhou (CN)

(73) Assignee: Hepagene Therapeutics (HK) Limited, Hong Kong (CN)

( * ) Notice: Subject to any disclaimer, the term of this patent is extended or adjusted under 35 U.S.C. 154(b) by 261 days.

(21) Appl. No.: 17/636,331

(22) PCT Filed: Oct. 19, 2020

(86) PCT No.: PCT/CN2020/121801
§ 371 (c)(1),
(2) Date: Feb. 17, 2022

(87) PCT Pub. No.: WO2021/032218
PCT Pub. Date: Feb. 25, 2021

(65) Prior Publication Data
US 2022/0298187 A1    Sep. 22, 2022

(30) Foreign Application Priority Data

Aug. 19, 2019  (CN) .......................... 201910763932.4
Feb. 24, 2020  (CN) .......................... 202010112084.3

(51) Int. Cl.
C07F 9/6574  (2006.01)
C07F 9/38    (2006.01)
C07F 9/40    (2006.01)
C07F 9/44    (2006.01)

(52) U.S. Cl.
CPC .......... *C07F 9/65742* (2013.01); *C07F 9/383* (2013.01); *C07F 9/4018* (2013.01); *C07F 9/4465* (2013.01)

(58) Field of Classification Search
CPC .... C07F 9/65742; C07F 9/383; C07F 9/4018; C07F 9/4465
USPC ......................................................... 514/101
See application file for complete search history.

(56) References Cited

FOREIGN PATENT DOCUMENTS

| JP | 2008-542301 A | 11/2008 |
| JP | 2019-531346 A | 10/2019 |
| WO | WO-2003/094845 A2 | 11/2003 |
| WO | WO-2005/051298 A2 | 6/2005 |
| WO | WO-2006/128055 A2 | 11/2006 |
| WO | WO-2006/128058 A2 | 11/2006 |
| WO | WO-2007/009913 A1 | 1/2007 |
| WO | WO-2010/122980 A1 | 10/2010 |
| WO | WO-2011/038207 A1 | 3/2011 |
| WO | WO-2014/183462 A1 | 11/2014 |
| WO | WO-2018/053036 A1 | 3/2018 |
| WO | WO-2019/005816 A1 | 1/2019 |

OTHER PUBLICATIONS

Examination Report on GB Application No. GB2203803.8 Dtd Feb. 23, 2023, 2 pages.
International Search Report and Written Opinion in PCT/CN2020/121801 on Jan. 4, 2021, 13 pages (including translation of Search Report).
Chinese Office Action on CN Application No. 202010112084.3 dated Apr. 12, 2022 including English translation (9 pages).
Extended European Search Report on EP 20854987 Dtd Nov. 30, 2023, 7 pages.
English translation of Office Action for JP 2002-509026 dated Jul. 30, 2024, 2 pages.

*Primary Examiner* — Kristin A Vajda
(74) *Attorney, Agent, or Firm* — Foley & Lardner LLP

(57) ABSTRACT

A chemical compound shown in formula (I) below and an isomer thereof or a pharmaceutically acceptable salt thereof. The compound improves THR-β agonistic activity while also improving selectivity for THR-α, thereby improving pharmaceutical quality.

24 Claims, No Drawings

HETEROCYCLIC THR-β RECEPTOR AGONIST COMPOUND AND PREPARATION METHOD AND USE THEREFOR

This application is the U.S. National Stage of International Patent No. PCT/CN2020/121801, filed Oct. 19, 2020, which claims priority to Chinese application number 201910763932.4, filed with the State Intellectual Property Office of the People's Republic of China on Aug. 19, 2019, and Chinese application number 202010112084.3, filed with the State Intellectual Property Office of the People's Republic of China on Feb. 24, 2020, the disclosures of which are incorporated herein by reference.

TECHNICAL FIELD

The present invention relates to the field of pharmaceutical synthesis, and, in particular, to a compound that may be used as a novel THR-β receptor agonist, and a preparation method and use therefor.

BACKGROUND ART

A thyroid hormone (TH) is synthesized in the thyroid in response to thyroid-stimulating hormone (TSH) secreted by the pituitary gland. Thyroid hormones play a crucial role in regulating body growth, development, and metabolism, and in maintaining a matrix balance. Thyroid hormones are mainly divided into two types: 3,3',5-triiodo-L-thyronine (T3) and prohormone thyroxine (T4). The human body mainly secretes T4, and in peripheral organs, T4 is converted by deiodinase into T3 that has higher activity. T3 and T4 produced by the thyroid are under the control of negative feedback, and thyroid-stimulating hormone (TSH) is responsible for performing normal thyroid functions and secreting thyroid hormones. Thyroid-stimulating hormone is synthesized in the anterior lobe of the pituitary gland, and its secretion is controlled by thyroid releasing hormone (TRH) synthesized in the hypothalamus.

Thyroid hormones perform functions by binding to thyroid hormone receptors (THRs). Thyroid hormone receptors, which are nuclear receptors, regulate the expression of target genes. Thyroid hormone receptors are divided into two subtypes: THR-α and THR-β. THR-α, mainly present in heart tissue, plays an important role in regulating the function of the heart. The THR-β subtype, mainly expressed in the liver and the pituitary gland, regulates the metabolism of cholesterol and the secretion of thyroid-stimulating hormone.

At normal levels, the thyroid hormone THs maintains body weight, metabolic rate, body temperature, AND emotion, and regulates serum cholesterol. Attempts have been made to regulate serum cholesterol by thyroid hormones. However, a natural thyroid hormone, when taken, produces side effects (such as tachycardia and arrhythmia, heart failure, and causing the thyroid axis function, muscle metabolism and osteoporosis) on the heart, and therefore cannot be used to treat hypercholesterolemia or obesity. Animal studies on selective knockout of the THR gene, as well as some studies on selective THR ligands, showed that the cardiac side effects caused by these thyroid hormones are attributable to THR-α.

The thyroid hormone receptor pathway regulates lipid metabolism, including metabolism of cholesterol, triglycerides, and lipoproteins. It has been clinically revealed that reducing low-density cholesterol will decrease the incidence of cardiovascular and cerebrovascular diseases.

Nonalcoholic fatty liver disease (NAFLD) is also a type of metabolic disorder caused by excessive accumulation of triglycerides in the liver, which can further cause liver cell damage and inflammation, leading to non-alcoholic steatohepatitis (NASH). NASH patients usually also have type 2 diabetes, hypercholesterolemia, hyperlipemia, and obesity. There is a high probability that a NASH patient will develop liver cirrhosis, liver failure, and ultimately liver cancer. No drug is available for effective treatment of NASH. As thyroid hormone performs the function of regulating lipid metabolism, the thyroid receptor pathway has become a potential target for the treatment of NASH and NAFLD. Animal in vivo studies have confirmed that thyroid hormone analogs can significantly reduce the degree of liver fat in animals.

A selective THR-β agonist may be used to avoid cardiac side effects caused by a conventional THR receptor agonist, selectively activating only THR-β only, which improves lipid metabolism of the cell, and performs the function of lowering cholesterol and blood lipids. However, a selective THR-β agonist may also inhibit the thyroid axis, causing side effects such as depression, fatigue, and osteoporosis. Therefore, it is necessary to develop a selective THR-β agonist that activates THR-β but mitigates the inhibitory effect on the thyroid axis, thereby avoiding side effects associated with thyroid axis inhibition.

Patents including WO03094845, WO2007009913, WO2010122980, and WO2011038207 disclose some THR receptor agonists whose structures are almost all designed and developed on the basis of T3, a natural ligand of a THR receptor. Against these backgrounds, a need still exists to develop a selective THR-β receptor agonist that brings about the beneficial effects of a thyroid hormone while avoiding adverse cardiac side effects.

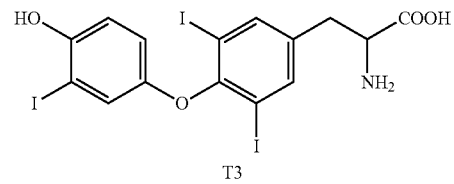

T3

Patent WO2005051298 also discloses some THR receptor agonists, among which a good compound (MB07444) has the following structure:

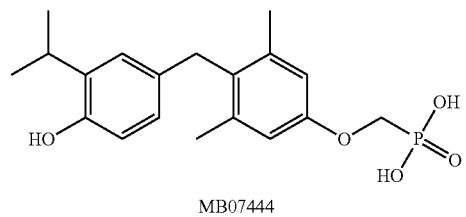 [SMILES: Cc1cc(OCP(=O)(O)O)cc(C)c1Cc1ccc(O)c(C(C)C)c1]

MB07444

Patent WO2006128058 also discloses some THR receptor agonists, among which several naphthol heterocyclic compounds have the following structure. However, the patent does not disclose any structure or embodiment similar to a compound of the present invention.

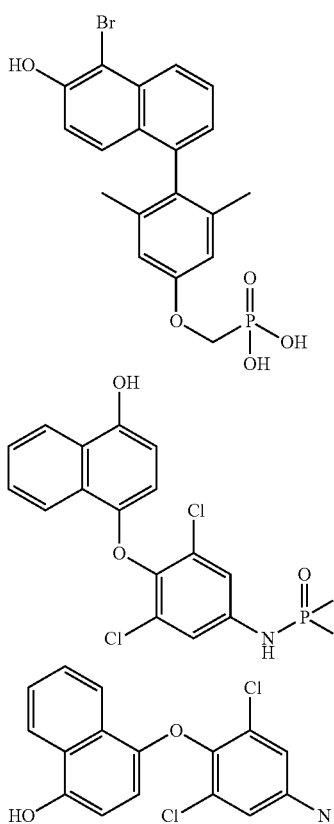

In the present invention, structural modification was performed on the basis of T3, a natural ligand of a THR receptor, and the inventors unexpectedly discovered that after the structure of the naphthol part was modified, some compounds unexpectedly improved the agonistic activity of a THR-receptor (compared with the code compound 7/MB07444 disclosed by patent WO2005051298), and that almost all heterocyclic compounds have improved selectivity for THR-α (compared with MB07444). In addition, some compounds of the present invention may be highly enriched in liver target organs after being modified by prodrugs, which further reduces distribution thereof in cardiac organs, thereby potentially reducing clinical side effects.

SUMMARY OF THE INVENTION

In order to solve the above-described technical problems, the present invention adopts the following technical solution:

According to one aspect of the present invention, the present invention provides a compound shown in formula (I) below and an isomer thereof or a pharmaceutically acceptable salt thereof,

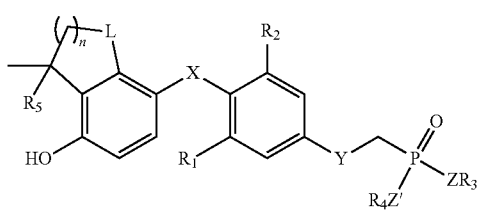

(I)

wherein
R$_1$ and R$_2$ are each independently selected from a halogen atom or a C$_{1-6}$ alkyl group;
R$_3$ and R$_4$ are each independently selected from hydrogen, a C$_{1-6}$ alkyl group, an unsubstituted phenyl group, a phenyl group substituted with at least one substituent selected from a halogen atom, a trifluoromethyl group, a C$_{1-6}$ alkyl group, a C$_{1-6}$ alkoxyl group or a cyano group, an unsubstituted naphthyl group, a naphthyl group substituted with at least one substituent selected from a halogen atom, a trifluoromethyl group, a C$_{1-6}$ alkyl group, a C$_{1-6}$ alkoxyl group or a cyano group,

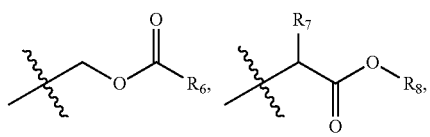

or R$_3$, R$_4$, and adjacent

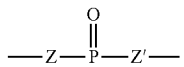

jointly form the following six-membered ring

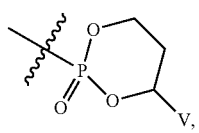

wherein V is an unsubstituted five-to ten-membered aryl group, a five-to ten-membered aryl group substituted with at least one substituent selected from a halogen atom, a trifluoromethyl group, a C$_{1-6}$ alkyl group, a C$_{1-6}$ alkoxyl group or a cyano group, an unsubstituted five-to ten-membered heteroaryl group containing 1 or 2 heteroatoms selected from N, S and O, a five-to ten-membered heteroaryl group that is substituted with at least one substituent selected from a halogen atom, a trifluoromethyl group, a C$_{1-6}$ alkyl group, a C$_{1-6}$ alkoxyl group or a cyano group and that contains one or two heteroatoms selected from N, S and O;
R$_5$ is selected from a H or C$_{1-6}$ alkyl group;
R$_6$, R$_7$, and R$_8$ are each independently selected from a C$_{1-6}$ alkyl group;
X is selected from —O— or —CH$_2$—;
Y is selected from —O— or —CH$_2$—;
Z and Z' are each independently selected from —O— or —NH—;
L is selected from —O—, —S— or —CH$_2$—
n is 1, 2 or 3;
the halogen atom is selected from F, Cl or Br.
According to another aspect of the present invention, preferably, in the structure shown in formula (I), R$_1$ and R$_2$ are each independently selected from F, Cl, Br or —CH$_3$.
Further preferably, R$_1$ and R$_2$ are both Cl.
Alternatively, preferably R$_1$ and R$_2$ are both -CH$_3$.
According to another aspect of the present invention, preferably, in the structure shown in formula (I), R$_5$ is selected from H or —CH$_3$; according to another aspect of the present invention, preferably, in the structure shown in formula (I), n is 1 or 2; further preferably, n is 1;

According to another aspect of the present invention, preferably, in the structure shown in formula (I), X is —CH$_2$—;

According to another aspect of the present invention, preferably, in the structure shown in formula (I), Y is —O—;

Preferably, in the structure shown in formula (I), V is an unsubstituted phenyl group, a phenyl group substituted with at least one substituent selected from a halogen atom, a trifluoromethyl group, a C$_{1-3}$ alkyl group and a C$_{1-3}$ alkoxyl group, an unsubstituted five-to six-membered monocyclic heteroaryl group containing 1 or 2 heteroatoms selected from N, S and O, a five-to six-membered monocyclic heteroaryl group that is substituted with at least one substituent selected from a halogen atom, a trifluoromethyl group, a C$_{1-3}$ alkyl group and an alkoxyl group and that contains 1 or 2 heteroatoms selected from N, S, and O.

According to another aspect of the present invention, preferably, the compound shown in formula (I) and an isomer thereof or a pharmaceutically acceptable salt thereof have a structure shown in formula (II) below:

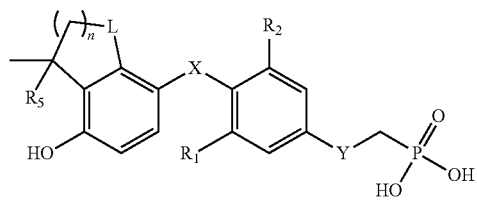

(II)

wherein
R$_1$, R$_2$, R$_5$, X, Y, and n are as defined in the preceding formula (I);
further preferably, in the structure shown in formula (II),
R$_1$ and R$_2$ are both —CH$_3$;
R$_5$ is selected from —CH$_3$;
X is —CH$_2$—;
Y is —O—;
L is —CH$_2$—;
n is 1 or 2.

According to another aspect of the present invention, preferably, the compound shown in formula (I) and an isomer thereof or a pharmaceutically acceptable salt thereof have a structure shown in formula (III):

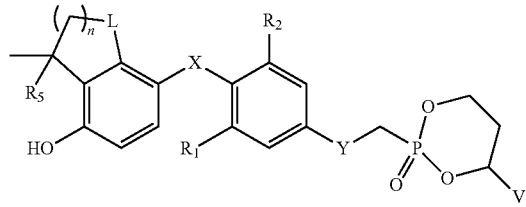

(III)

wherein
R$_1$, R$_2$, R$_5$, X, Y, L, n, and V are as defined in the preceding formula (I);
further preferably, in the structure shown in formula (II),
R$_1$ and R$_2$ are both —CH$_3$;
R$_5$ is selected from —CH$_3$;
X is —CH$_2$—;
Y is —O—;
L is —CH$_2$—;
n is 1 or 2;
preferably, V is an unsubstituted phenyl group, a phenyl group substituted with at least one substituent selected from a halogen atom, a trifluoromethyl group, a C$_{1-3}$ alkyl group and a C$_{1-3}$ alkoxyl group, a pyridyl group, and a pyridyl group substituted with at least one substituent selected from a halogen atom, a trifluoromethyl group, a C$_{1-3}$ alkyl group, and a C$_{1-3}$ alkoxyl group.

Further preferably, V is an m-chlorophenyl group.

According to another aspect of the present invention, preferably, the compound shown in formula (I) and an isomer thereof or a pharmaceutically acceptable salt thereof have a structure shown in formula (IV):

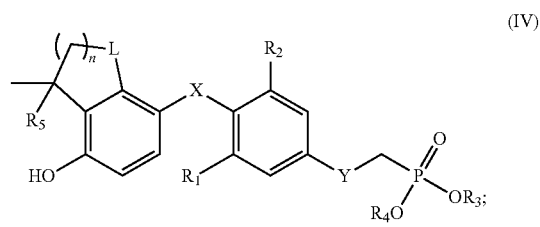

(IV)

wherein
R$_1$, R$_2$, R$_5$, X, Y, L, and n are as defined in the preceding formula (I);
R$_3$ and RA are each independently selected from a C$_{1-6}$ alkyl group, a phenyl group, a phenyl group substituted with at least one substituent selected from a halogen atom, a trifluoromethyl group, a C$_{1-6}$ alkyl group, a C$_{1-6}$ alkoxyl group or a cyano group, a naphthyl group, a naphthyl group substituted with at least one substituent selected from a halogen atom, a trifluoromethyl group, a C$_{1-6}$ alkyl group, a C$_{1-6}$ alkoxyl group or a cyano group,

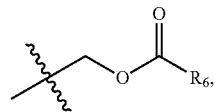

wherein R$_6$ is selected from a C$_{1-6}$ alkyl group;
further preferably, in the structure shown in formula (IV),
R$_1$ and R$_2$ are both-CH$_3$;
R$_5$ is selected from—CH$_3$;
X is —CH$_2$—;
Y is —O—;
L is —CH$_2$—;
n is 1 or 2;
R$_3$ and R$_4$ are both

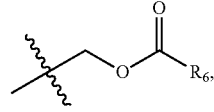

wherein R$^6$ is a C$_{1-6}$ alkyl group;

more preferably, both $R_3$ and $R_4$ are

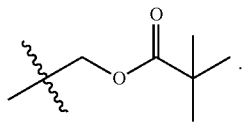

According to another aspect of the present invention, preferably, the compound shown in formula (I) and an isomer thereof or a pharmaceutically acceptable salt thereof have a structure shown in formula (V):

(V)

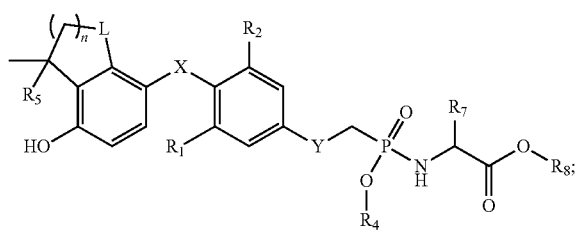

wherein $R_1$, $R_2$, $R_5$, X, Y, L, and n are as defined in the preceding formula (I);

$R_4$ is selected from a $C_{1-6}$ alkyl group, a phenyl group, a phenyl group substituted with at least one substituent selected from a halogen atom, a trifluoromethyl group, a $C_{1-6}$ alkyl group, a $C_{1-6}$ alkoxyl group or a cyano group, a naphthyl group, a naphthyl group substituted with at least one substituent selected from a halogen atom, a trifluoromethyl group, a $C_{1-6}$ alkyl group, a $C_{1-6}$ alkoxyl group or a cyano group, $R_7$ and $R_8$ are each independently selected from a $C_{1-6}$ alkyl group;

further preferably, in the structure shown in formula (V), $R_1$ and $R_2$ are both —$CH_3$;

$R_5$ is selected from —$CH_3$;

X is —$CH_2$—;

Y is —O—;

L is —$CH_2$—;

n is 1 or 2;

$R_4$ is a phenyl group or a naphthyl group;

$R_7$ is a methyl group;

$R_8$ is an ethyl group or an isopropyl group;

according to another aspect of the present invention, preferably, the compound and a pharmaceutically acceptable salt and prodrug thereof are one of the following compounds:

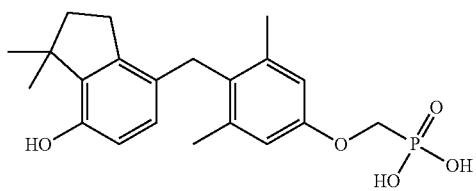

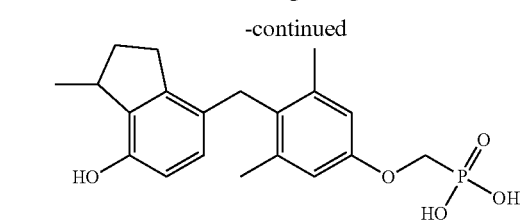

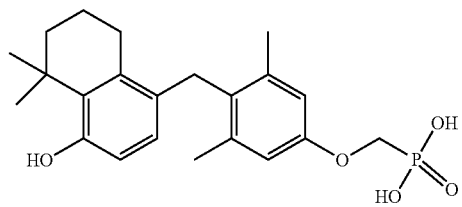

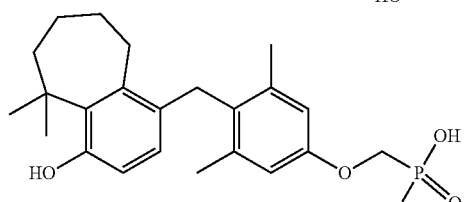

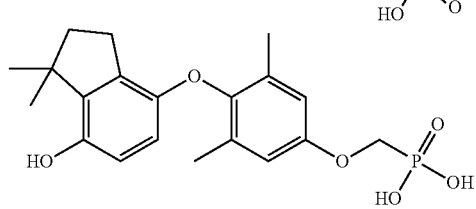

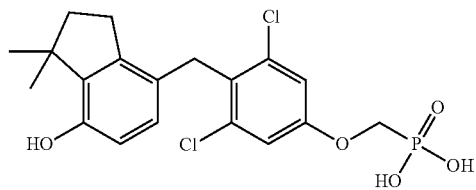

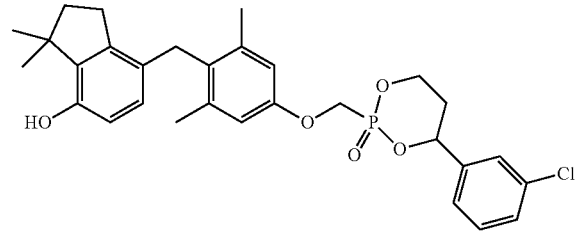

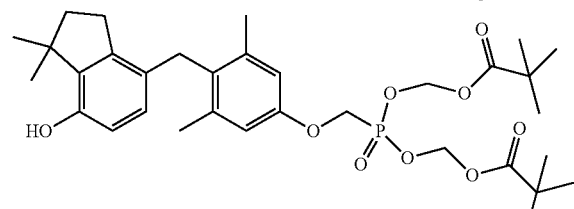

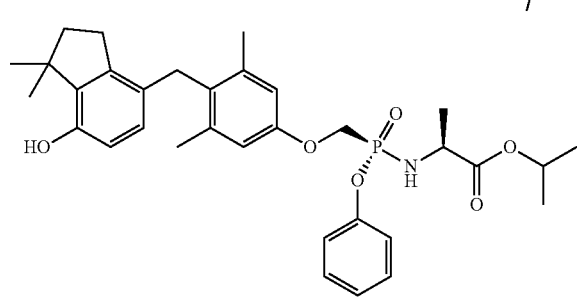

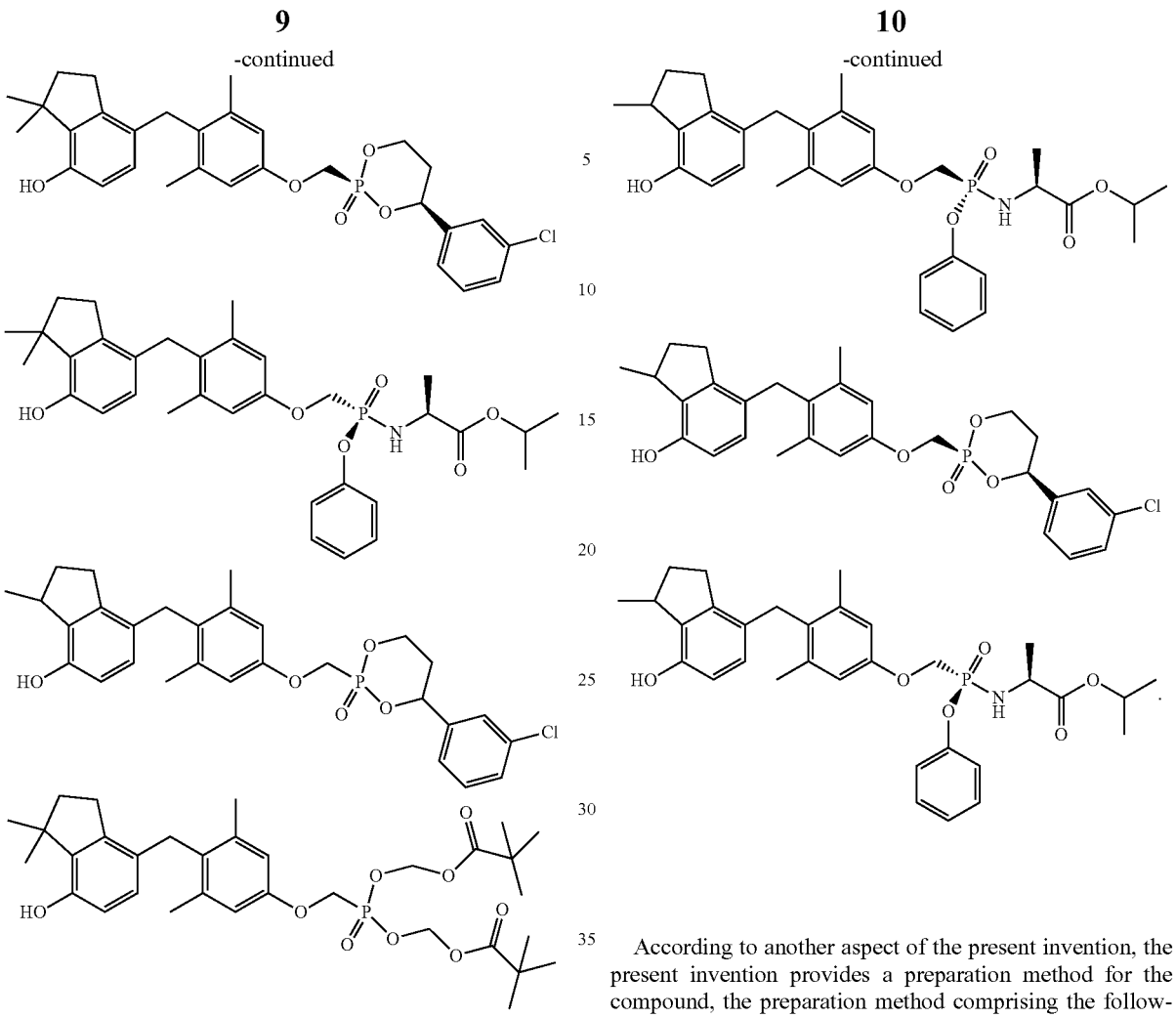
According to another aspect of the present invention, the present invention provides a preparation method for the compound, the preparation method comprising the following steps:
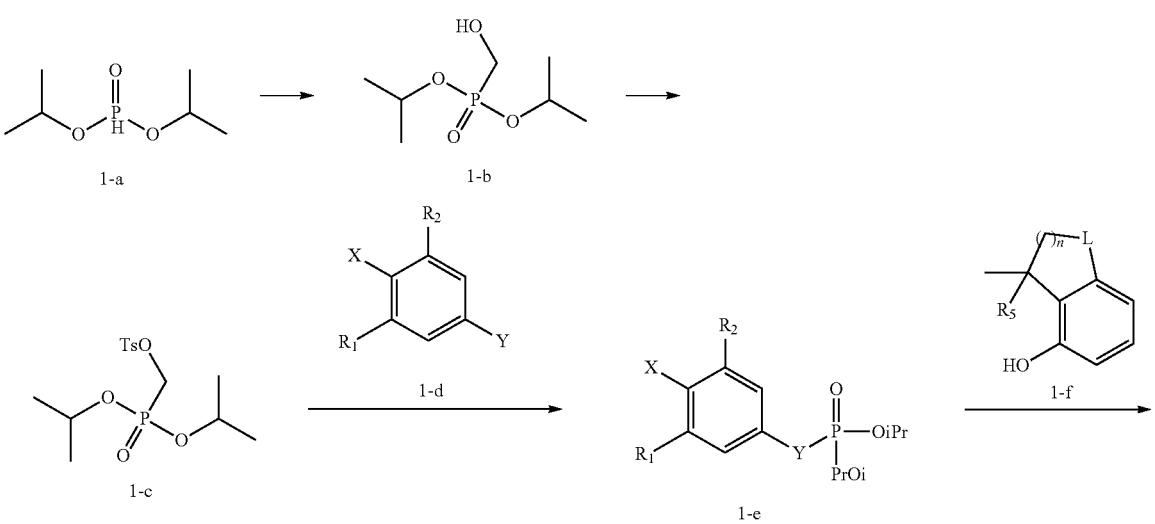

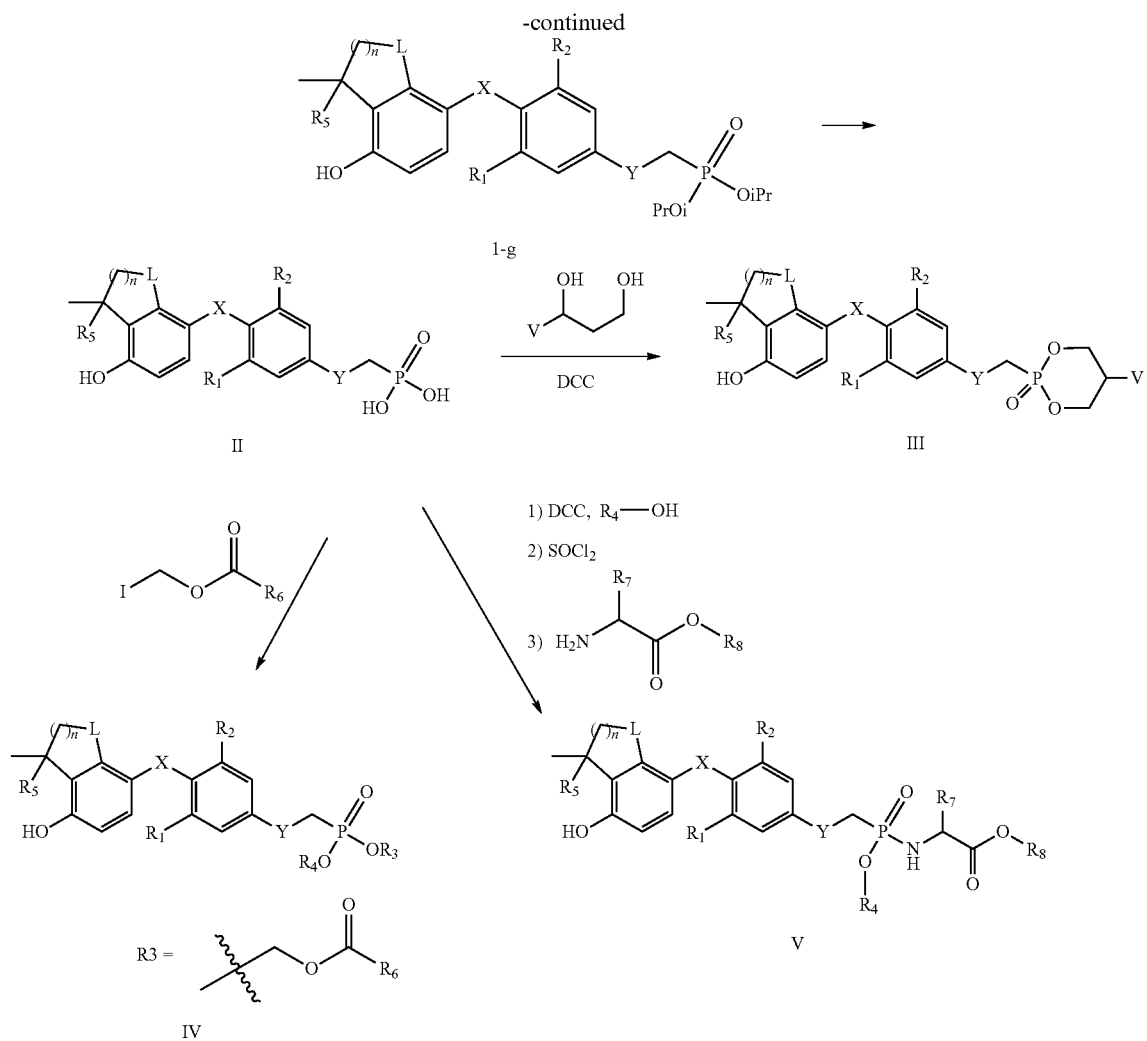

1) Add paraformaldehyde and potassium carbonate to isopropanol, slowly add diisopropyl phosphite dropwise when the temperature has been raised to 50 degrees Celsius, and stir for 2 hours maintaining a temperature of 50 degrees Celsius. After post-treatment, the compound of general formula 1-b is obtained;

2) Add compound 1-b and triethylamine to dichloromethane separately, and cool the system by 4 degrees Celsius with an ice bath. While stirring, slowly add dropwise a p-toluenesulfonyl chloride solution into the reaction liquid with a dropping funnel and, after completion of the dropping, continue stirring for 2 hours while keeping the ice bath. After completion of the reaction, the active ester 1-c is obtained after post-treatment;

3) Add compound 1-c to a mixture of dimethyl sulfoxide, compound 1-d, and cesium carbonate, raise the temperature to 55 degrees Celsius in a nitrogen atmosphere, and stir for 6 hours for reaction to obtain a compound of general formula 1-e;

4) Add compound 1-e to a dichloromethane solution of compound 1-f, cool the system to 4 degrees Celsius with an ice bath, and add a trifluoroacetic acid dropwise to catalyze the reaction. After post-treatment, a compound of general formula 1-g is obtained;

5) Add trimethylchlorosilane dropwise to an acetonitrile solution of compound 1-g and of potassium iodide, raise the temperature to 50° C., and stir for 2 hours for reaction. After dealkylation, phosphoric acid compound II is obtained;

6) Dissolve the phosphoric acid compound II and 1-(3-chlorophenyl) propane-1,3-diol in pyridine and DMF, and add condensation reagent DCC at room temperature. Heat to 70° C. and stir for 4 hours, and a prodrug compound III of II is obtained after post-treatment.

7) Alternatively, add diisopropylethylamine to an acetonitrile solution of phosphoric acid compound II at room temperature. Heat to 40° C., stir for half an hour, add iodine, and continue to stir overnight. A diesterization reaction occurs to generate phosphate ester prodrug IV.

8) Alternatively, react phosphoric acid compound II with phenol or naphthol $R_4$—OH under the promotion by the condensation reagent DCC, and an acyl chloride intermediate is generated from the sulfonyl chloride and then is reacted with an amino acid ester to obtain prodrug compound V of II.

Each of the substituents $R_1$, $R_2$, $R_3$, $R_4$, $R_5$, $R_6$, $R_7$, $R_8$, X, Y, L, n, and V in the preceding reaction formula are as defined in the preceding formula (I).

According to another aspect of the present invention, the present invention provides a use of the compound in the preparation of a drug for treating a metabolism-related disease or fibrosis —related disease.

According to another aspect of the present invention, the present invention provides a pharmaceutical composition comprising a therapeutically effective amount of the compound according to the present invention and a pharmaceutically acceptable salt thereof as active ingredients, and a pharmaceutically acceptable excipient.

Preferably, the metabolism-related disease is selected from: obesity, hyperlipidemia, hypercholesterolemia, diabetes, and non-alcoholic steatohepatitis (NASH), hepatic steatosis, atherosclerosis, hypothyroidism and thyroid cancer, liver fibrosis, pulmonary fibrosis; preferably, the metabolism-related disease is selected from: non-alcoholic steatohepatitis (NASH), hypothyroidism and thyroid cancer, liver fibrosis, pulmonary fibrosis.

According to another aspect of the present invention, the present invention provides a method for treating a metabolism-related disease, the method comprising administering to a subject an effective amount of the compound according to the present invention or a pharmaceutical composition comprising the compound and a pharmaceutically acceptable salt thereof as active ingredients.

Preferably, according to the method for treating a metabolism-related disease, the metabolism-related disease is selected from: obesity, hyperlipidemia, hypercholesterolemia, diabetes, and non-alcoholic steatohepatitis (NASH), hepatic steatosis, atherosclerosis, hypothyroidism and thyroid cancer; preferably, the metabolism-related disease is selected from: non-alcoholic steatohepatitis (NASH), hypothyroidism, and thyroid cancer.

Preferably, according to another aspect of the present invention, a method for treating a metabolism-related disease or fibrosis —related disease is provided, the method comprising administering to a subject an effective amount of the compound according to the present invention or a pharmaceutical composition containing the compound and an isomer thereof or a pharmaceutically acceptable salt thereof as active ingredients.

Specific Embodiments

The present invention will be described in detail below. Before the description is given, it should be understood that terms used in the description and the appended claims, instead of being construed as being limited to general meanings and dictionary meanings, should be explained according to meanings and concepts corresponding to the technical aspects of the present invention on the basis of the principle of allowing the inventors to appropriately define terms for optimal explanation. Therefore, the description provided herein is only preferred embodiments given for illustrative purposes, instead of being intended to limit the scope of the present invention, and, therefore, it should be understood that other equivalent embodiments or improved embodiments may be derived therefrom without departing from the spirit or scope of the present invention.

According to the present invention, unless otherwise stated, all terms cited herein have the same meanings as the terms as commonly understood by those of ordinary skill in the art.

For example, the term "salt" as used herein refers to a compound containing cations and anions, which may be produced by protonation of proton-acceptable sites and/or deprotonation of proton-available sites. It is noteworthy that protonation of proton-acceptable sites leads to the formation of cationic substances whose charge is balanced by the presence of physiological anions, while deprotonation of proton-available sites leads to the formation of anionic substances whose charge is balanced by the presence of physiological cations.

The term "pharmaceutically acceptable salt" means that the salt is acceptable in relation to pharmacy. Examples of pharmaceutically acceptable salts include, but are not limited to: (1) acid addition salts, formed with inorganic acids, such as hydrochloric acid, hydrobromic acid, sulfuric acid, nitric acid, and phosphoric acid; or formed with organic acids, such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4 paratoluenesulfonic acid, camphor acid, lauryl sulfuric acid, gluconic acid, glutamic acid, salicylic acid, and cis —adipenedioic acid; or (2) base addition salts, formed with a conjugate base of any of the above-mentioned inorganic acids, wherein the conjugate base contains a cationic component selected from Na+, K+, $Mg^{2+}$, $Ca^{2+}$, and $NH_xR_{4x}^+$, wherein $NH_xR_{4-x}^+$ (R is a $C_{1-4}$ alkyl group, and the subscript x is an integer selected from 0, 1, 2, 3, or 4) represents the cation in the quaternary ammonium salt. It should be understood that all pharmaceutically acceptable salts involved include the solvent addition form (solvate) or crystal form (polymorph) of the same acid addition salt defined herein.

The term "$C_{1-M}$ alkyl group" refers to an alkyl group containing 1-M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30, for example. For example, the term "$C_{1-6}$ alkyl group" refers to an alkyl group containing 1-6 carbon atoms. Examples of alkyl groups include, but are not limited to, lower alkyl groups, including methyl group, ethyl group, propyl group, isopropyl group, n-butyl group, isobutyl group, tert-butyl or pentyl group, isopentyl group, neopentyl group, hexyl group, heptyl group and octyl group.

The term "aryl group" refers to an aromatic system that can be a single ring or polyaromatic rings originally fused or connected together, so that at least a part of the fused or connected rings form a conjugated aromatic system. Aryl groups include, but are not limited to: phenyl group, naphthyl group, and tetrahydronaphthyl group. An aryl group may be optionally substituted, such as an aryl or heterocyclic group which may be substituted with 1-4 groups selected from the group consisting of halogen, —CN, —OH, —$NO_2$, amino group, alkyl group, cycloalkyl group, alkenyl group, alkynyl group, alkoxyl group, aryloxyl group, substituted alkoxyl group, alkylcarbonyl group, alkylcarboxyl group, alkylamino group, or arylthio group.

The term "substituted" means that a reference group is substitutable with one or more additional groups, the additional groups being individually and independently selected from alkyl group, cycloalkyl group, aryl group, heteroaryl group, heteroalicyclic hydrocarbon, hydroxyl group, alkoxyl group, alkylthio group, arylthio group, alkylsulfoxyl group, arylsulfoxyl group, alkylsulfuryl group, arylsulfuryl group, cyano group, halogroup, carbonyl group, thiocarbonyl group, nitro group, haloalkyl group, fluoroalkyl group and amino group, including mono- and di-substituted amino groups and protected derivatives thereof.

A compound shown in formula (I) or a pharmaceutically acceptable salt thereof, and a pharmaceutical composition containing the compound provided by the present invention may be in various forms, such as tablets, capsules, powders, syrups, solutions, and suspensions and aerosols, and may be present in a suitable solid or liquid carrier or diluent and in a suitable sterilizer for injection or drip infusion.

Various dosage forms of a pharmaceutical composition of the present invention may be prepared by conventional preparation methods in the pharmaceutical field. For example, the unit dose of the pharmaceutical formulation contains 0.05-200 mg of the compound of formula (I) or a pharmaceutically acceptable salt thereof, wherein, preferably, the unit dose of the pharmaceutical formulation contains 0.1 mg-100 mg of the compound of formula (I).

The compound and pharmaceutical composition shown in general formula (I) of the present invention may be used clinically in mammals, including humans and animals, and may be administered orally, nasally, percutaneously, pulmonarily, or through the gastrointestinal tract. Oral administration is the most preferred. The most preferred daily dose is 0.01-200 mg/kg body weight, taken at one time, or 0.01-100 mg/kg body weight in split doses. Regardless of the adopted method of administration, the optimal dose for an individual should be determined on the basis of specific treatment. Generally, a small dose should be taken at the beginning, and then the dose may be increased gradually until the most suitable dose is found.

In the present invention, the term "effective amount" may refer to an effective amount for the dosage and time period required to achieve a desired effect. The effective amount may vary depending on certain factors, such as type of disease or condition of disease during treatment, structure of specific target organ of administration, patient's stature, or severity of disease or of symptom. Those of ordinary skill in the art can empirically determine the effective amount of a specific compound without conducting an excessive amount of experiments.

A typical formulation is prepared by mixing the compound shown in general formula (I) of the present invention, a carrier, a diluent, or an excipient. Suitable carriers, diluents or excipients are well known to those of ordinary skill in the art, and include substances such as carbohydrates, waxes, water-soluble and/or inflatable polymers, hydrophilic or hydrophobic substances, gelatin, oils, solvents, and water.

A specific carrier, diluent or excipient to be used will depend on the method of and purpose of use of the compound of the present invention. Solvents are generally selected on the basis of solvents that those of ordinary skill in the art believe may be safely and effectively administered to mammals. Generally, safe solvents are nontoxic aqueous solvents, such as water, and other nontoxic solvents that are soluble in or miscible with water. Suitable aqueous solvents include one or more of water, ethanol, propylene glycol, and polyethylene glycol (such as PEG400 and PEG300). The formulation may also comprise one or more buffers, stabilizers, surfactants, wetting agents, lubricants, emulsifiers, suspending agents, preservatives, antioxidants, sunscreens, glidants, processing aids, coloring agents, sweetening agents, perfuming agents, flavoring agents or other known additives, so that the drug may be manufactured or used in an acceptable form.

When the compound of formula (I) according to the present invention is used in combination with at least one other drug, the two or more drugs may be used separately or in combination, and are preferably administered in the form of a pharmaceutical composition. The compound or pharmaceutical composition of formula (I) of the present invention may be administered separately or together to a subject in any known form of medication, for example, oral administration, intravenous injection, rectal administration, vaginal administration, cutaneous permeation, or another form of topical or systemic administration.

These pharmaceutical compositions may also contain one or more buffers, stabilizers, surfactants, wetting agents, lubricants, emulsifiers, suspending agents, preservatives, antioxidants, sunscreens, glidants, processing agents, coloring agent, sweetening agent, perfuming agents, flavoring agents or other known additives, so that the pharmaceutical composition may be manufactured or used in an acceptable form.

A drug of the present invention is preferably administered orally. Solid dosage forms for oral administration may include capsules, tablets, powder or granular formulations. In a solid dosage form, the compound or pharmaceutical composition of the present invention is mixed with at least one inert excipient, diluent or carrier. Suitable excipients, diluents or carriers include substances such as sodium citrate or dicalcium phosphate, or starch, lactose, sucrose, mannitol, and silicic acid; binders such as carboxymethyl cellulose, alginate, gelatin, polyvinylpyrrolidone, sucrose, and gum arabic; wetting agents such as glycerin; disintegrants such as agar, calcium carbonate, potato starch or tapioca, alginic acid, specific complex silicate, and sodium carbonate; solution blockers such as paraffin; absorption enhancers such as quaternary ammonium compounds; adsorbents such as kaolin and bentonite; lubricants such as talc, calcium stearate, magnesium stearate, solid polyethylene glycol, and sodium lauryl sulfate. In the case of capsules and tablets, the dosage form may also comprise a buffering agent. Similar types of solid compositions may also be used as fillers in soft and hard filled gelatin capsules, in which lactose, high-molecular-weight polyethylene glycol, etc. are used as excipients.

Liquid dosage forms for oral administration include pharmaceutically acceptable emulsions, solutions, suspensions, syrups and elixirs. In addition to the compound of the present invention or a pharmaceutical composition thereof, the liquid dosage form may contain an inert diluent commonly used in the art, such as water or another solvent; solubilizers and emulsifiers such as ethanol, isopropyl alcohol, ethyl carbonate, ethyl acetate, benzyl alcohol, benzyl benzoate, propylene glycol, 1,3-butanediol, dimethylformamide; oils (such as cottonseed oil, peanut oil, corn germ oil, olive oil, castor oil, and sesame oil); glycerin; tetrahydrofurfuryl alcohol; fatty acid esters of polyethylene glycol and sorbitan; or a mixture of a plurality of these substances, etc.

In addition to these inert diluents, the composition may also comprise excipients, such as one or more of a wetting agent, an emulsifier, a suspending agent, a sweetening agent, a flavoring agent, and a perfuming agent.

With regard to suspension, in addition to the compound shown in general formula (I) of the present invention or a pharmaceutically acceptable salt thereof or a pharmaceutical composition containing the same, it may further contain a carrier, for example, a suspending agent, such as ethoxylated isostearyl alcohol, polyoxyethylene sorbitol, sorbitan ester, microcrystalline cellulose, aluminum hydroxide, bentonite, agar and adragant, or a mixture of a plurality of these substances.

The compound shown in general formula (I) of the present invention or a pharmaceutically acceptable salt thereof or a pharmaceutical composition containing the same may be administered in other dosage forms for topical administration, including ointments, powders, sprays and inhalants. The drug may be mixed with a pharmaceutically acceptable excipient, diluent or carrier and any required preservatives, buffers or propellants under aseptic conditions. Ophthalmic formulations, ophthalmic ointments, powders and solutions are also intended to fall within the scope of the present invention.

In addition, the present disclosure further covers a kit (such as a pharmaceutical package). A provided kit may comprise a pharmaceutical composition or compound described herein and a container (for example, a vial, an ampoule, a bottle, a syringe and/or subpackage or another suitable container). In some embodiments, a provided kit may optionally further comprise a second container that contains a pharmaceutical excipient for diluting or suspending a pharmaceutical composition or compound described herein. In some embodiments, a pharmaceutical composition or compound combination described herein disposed in the first container and the second container forms a unit dosage form.

In some embodiments, a kit described herein further comprises instructions on how to use the compound or pharmaceutical composition included in the kit. A kit described herein may further comprise information required by regulatory agencies, such as the U.S. Food and Drug Administration (FDA). In some embodiments, information included in the kit is prescription information. In certain embodiments, a kit and instructions provide treatment of proliferative diseases in subjects in need thereof and/or prevention of proliferative diseases in subjects in need thereof. A kit described herein may contain one or more additional pharmaceutical preparations as separate compositions.

The present invention will be further described in detail below in conjunction with specific embodiments, but the present invention is not limited to the embodiments described below, the embodiments being intended to better explain some specific manifestations of the present invention, instead of being construed as limiting the scope of the present invention in any way. Conditions not specified in the embodiments are conventional conditions. Unless otherwise specified, the reagents and instruments used in the following embodiments are all commercially available products.

The structures of the compounds in the following embodiments were determined by nuclear magnetic resonance (NMR) or/and mass spectrometry (MS). The NMR shift (δ) was given in units of 10-6 (ppm). A Bruker AVANCE-400 nuclear magnetic instrument was used for NMR measurement, the solvents used were deuterated dimethyl sulfoxide (DMSO-d6), deuterated chloroform (CDCl3), and deuterated methanol (CD3OD), and the internal standard was tetramethylsilane (TMS).

MS measurement was performed with a FINNIGAN LCQAd (ESI) mass spectrometer (manufacturer: Thermo, model: Finnigan LCQ advantage MAX).

A Yantai Huanghai HSGF254 or Qingdao GF254 silica gel plate was used as the thin-layer chromatography silica gel plate, the specifications of the silica gel plate used in the thin-layer chromatography (TLC) was 0.15 mm-0.2 mm, and the specifications used for product separation and purification in the thin-layer chromatography was 0.4 mm-0.5 mm.

In column chromatography, Yantai Huanghai silica gel, which is 200-300 mesh silica gel, was generally used as the carrier.

Unless otherwise specified, in an embodiment, the reaction temperature was room temperature, in the range of 20 degrees Celsius-30 degrees Celsius.

In the detection of a reaction process in an embodiment, thin-layer chromatography (TLC) was adopted, wherein the developing solvent system used and the elution system of column chromatography used to purify the compound included: A: dichloromethane and methanol system, B: n-hexane and ethyl acetate system, C: petroleum ether and ethyl acetate system, and D: acetone and petroleum ether system, and the volume ratio between the solvents was adjusted according to the polarity of the compound.

Abbreviations used in the experiments are: DCC, dicyclohexylcarbodiimide; TMSI, trimethylsilyl iodide; EA, ethyl acetate; DCM, dichloromethane; h, hour; DMF, N,N-dimethylamide.

Reference embodiment A: Preparation of ((4-((4-hydroxynaphthyl-1-yl)methyl)-3,5-dimethylphenoxy) methyl) phosphoric acid

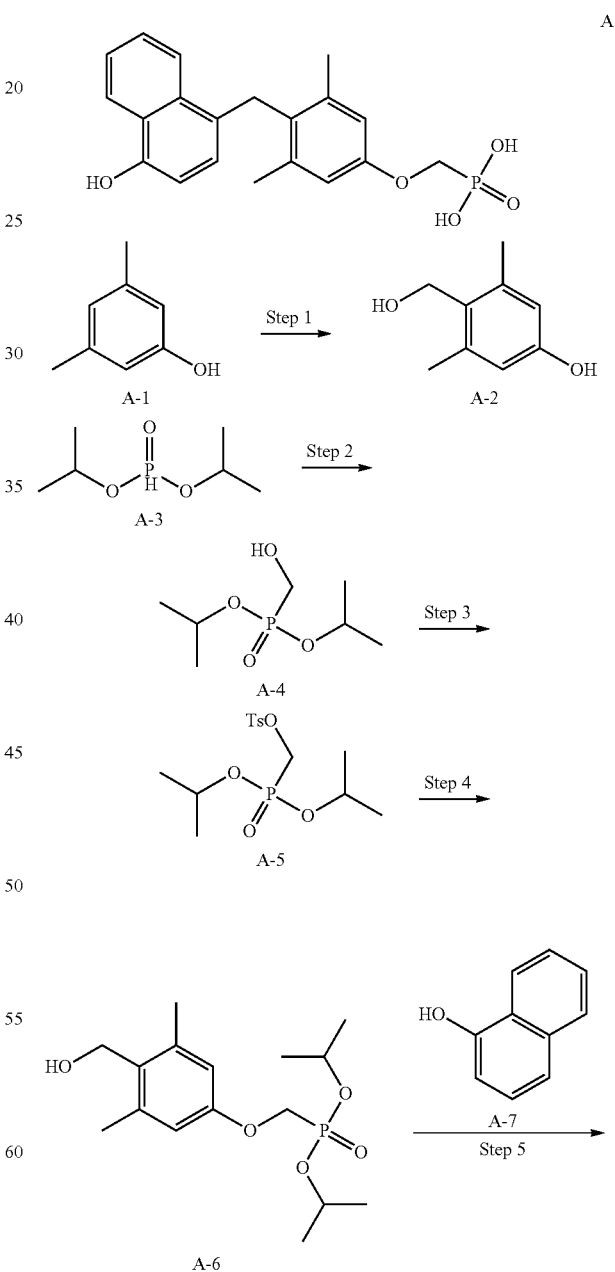

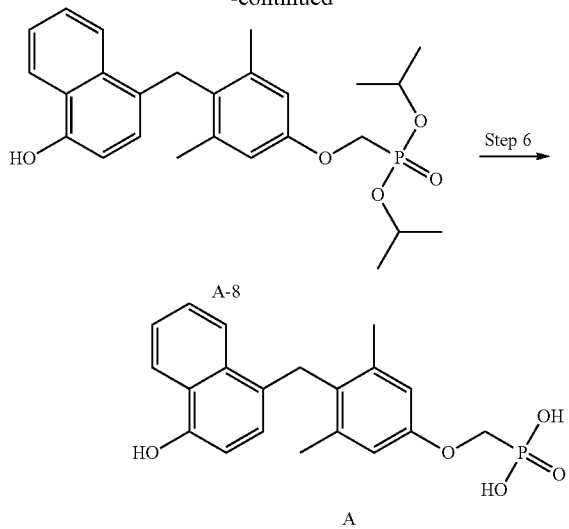

Step 1: Synthesis of 4-hydroxymethyl-3,5-dimethylphenol A-2

Compound A-1 (91.5 g, 750 mmol), water (525 ml), and a NaOH solution (30 ml) with a concentration of 50% by mass were mixed and stirred for 1 h until the mixture was completely clear. The temperature of the system was cooled to 4 degrees Celsius with an ice water bath, and a formaldehyde solution (50 g, 618 mmol) was added all at once. After stirring for 6 hours with the ice bath kept, the temperature was naturally raised to room temperature and stirring was performed for 12 hours. The reaction solution was poured into a mixed solution of dichloromethane (200 ml) and ethyl acetate (200 ml), concentrated HCl (56 ml) was added dropwise to reach pH 5, stirring was performed for another 6 h, and the precipitated solid was collected by filtration. The filter cake was washed with water (50 ml) and dichloromethane (75 ml), and dried to obtain a white solid A-2 (40 g).

$^1$H NMR (400 MHZ, CD$_3$OH): 6.47 (s, 2H), 4.60 (s, 2H), 2.34 (s, 6H).

Step 2: Synthesis of hydroxymethyl diisopropyl phosphate A-4

Paraformaldehyde (9 g, 326 mmol) and potassium carbonate were added to isopropanol (90 ml), diisopropyl phosphite (45.2 g, 272 mmol) was slowly added dropwise after the temperature was raised to 50 degrees Celsius, and stirring was performed for 2 hours with the temperature kept at 50 degrees Celsius. The temperature of the system was lowered to 35 degrees Celsius, filtration was performed, the filter cake was washed twice with isopropanol, and the filtrates were combined and concentrated under reduced pressure. Dichloromethane (180 ml) was added to the residue, washed with 1 N hydrochloric acid (27 ml) and saturated NaHCO$_3$ (45 ml), dried, and concentrated under reduced pressure to obtain colorless liquid A-4 (53.2 g).

$^1$H NMR (400 MHZ, CDCl$_3$): 6.53 (m, J=28.0 Hz, 2H), 4.60 (m, J=32.0 Hz, 2H), 3.64 (m, J=12.0 Hz, 2H), 1.24 (d, J=8.0 Hz, 12H).

Step 3: Synthesis of (Diisopropoxy Phosphate) Methyl-4-Methylbenzenesulfonate a-5

Compound A-4 (49 g, 250 mmol) and triethylamine (69.5 ml, 500 mmol) were added to dichloromethane (150 ml), and the system was cooled by 4 degrees Celsius in an ice bath. While stirring, a solution of p-toluenesulfonyl chloride (50 g, 263 mmol) in dichloromethane (350 ml) was slowly added dropwise with a dropping funnel into the reaction solution (with the temperature kept below 10 degrees Celsius), and, after completion of dropping, stirring was continued for 2 hours with the ice bath maintained. The reaction solution was washed with 1 M hydrochloric acid and saturated sodium bicarbonate aqueous solution (300 ml) and dried, and then the organic phase was concentrated under reduced pressure and purified by column chromatography to obtain colorless liquid A-5 (78 g).

$^1$H NMR (400 MHZ, CDCl$_3$): 7.80 (d, J=8.0 Hz, 2H), 7.36 (d, J=8.0 Hz, 2H), 4.78 (m, J=48.0 Hz, 2H), 4.17 (m, J=46.0 Hz, 3H), 2.30 (s, 1H), 1.32 (m, J=24.0 Hz, 12H).

Step 4: Synthesis of diisopropyl ((4-(hydroxymethyl)-3,5-dimethylphenoxy) methyl) phosphate A-6

Compound A-5 (35 g, 100 mmol) was added to a mixture of dimethyl sulfoxide (85 ml), compound A-2 (18 g, 120 mmol) and cesium carbonate (52 g, 160 mmol), the temperature was raised to 55 degrees Celsius under a nitrogen atmosphere, stirring was performed for 6 hours, and cooling was performed. Ethyl acetate (100 ml) and 1% sodium chloride aqueous solution (200 ml) were added to the system, the layers were separated, the organic phase was washed with saturated brine, and the organic phase was concentrated under reduced pressure to obtain brown oily substance A-6 (45 g).

$^1$H NMR (400 MHZ, CDCl$_3$): 6.62 (s, 2H), 4.85 (m, J=32.0 Hz, 2H), 4.66 (s, 2H), 4.16 (d, J=8.0 Hz, 2H), 2.39 (s, 6H), 1.37 (m, J=16.0 Hz, 12H).

Step 5: Synthesis of diisopropyl ((4-((4-hydroxynaphthalene-1-yl)methyl)-3,5-dimethylphenoxy) methyl) phosphate A-8

Compound A-7 (275 mg, 1.91 mmol) was added to compound A-6 (315 mg, 0.95 mmol) in dichloromethane (3 ml) solution, the system was cooled to 4 degrees Celsius with an ice bath, trifluoroacetic acid (326 mg, 2.86 mmol) was added dropwise, and the TLC dot plate tracking material A-6 disappeared. Water (5 ml) was added, the layers were separated, the organic phase was washed with water (5 ml), the organic phase was concentrated under reduced pressure to obtain a brown oily substance, ether (5 ml) was added, the ambient temperature was minus 18 degrees Celsius, a switch was made to room temperature 5 minutes later and stirring was performed for 1 hour, and a white solid A-8 (100 mg) was precipitated. $^1$H NMR (400 MHZ, CDCl$_3$): 8.32 (d, J=8.0 Hz, 1H), 8.18 (d, J=8.0 Hz, 1H), 7.63 (t, J=12.0 Hz, 1H), 7.56 (t, J=16.0 Hz, 1H), 6.71 (s, 2H), 6.43 (d, J=8.0 Hz, 2H), 4.91 (m, J=44.0 Hz, 2H), 4.26 (m, J=12.0 Hz, 4H), 2.15 (s, 6H), 1.40 (m, J=12.0 Hz, 12H).

Step 6: Synthesis of ((4-((4-hydroxynaphthyl-1-yl) methyl)-3,5-dimethylphenoxy) methyl) phosphoric acid A Trimethylchlorosilane (76 mg, 0.7 mmol) was added dropwise to a mixture of compound A-8 (100 mg, 0.22 mmol) and potassium iodide (116 mg, 0.70 mmol) in acetonitrile (1 ml), the temperature was raised to 50° C., and the reaction was stirred for 2 hours. Ethyl acetate (20 ml) and water (20 ml) were added, the layers were separated, the organic phase was washed with saturated brine (20 ml) 1 time, and the solvent was concentrated under reduced pressure to obtain a black solid. Water (12 ml) was added, the temperature was raised to 35-40° C., and the mixture was stirred for 30 minutes, filtered, and dried to obtain brown solid reference compound A (35 mg).

$^1$H NMR (400 MHZ, CDCl$_3$): 8.26 (d, J=8.0 Hz, 1H), 8.18 (d, J=8.0 Hz, 1H), 7.58 (t, J=16.0 Hz, 1H), 7.48 (t, J=20.0 Hz, 1H), 6.81 (m, J=16.0 Hz, 2H), 6.57 (d, J=8.0 Hz, 1H), 6.36 (d, J=8.0 Hz, 1H), 4.26 (s, 2H), 4.23 (d, J=9.0 Hz, 2H), 2.16 (s, 6H).

MS m/s (ESI): 371.1 [M−1].

Reference embodiment B: Preparation of ((4-((4-hydroxy-5,6,7,8-tetrahydronaphthalen-1-yl)methyl)-3,5-dimethylphenoxy) methyl) phosphoric acid.

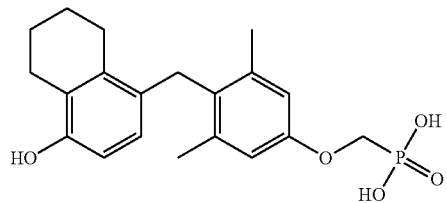

B

Using the route of synthesis of reference embodiment A, reference compound B may be obtained by replacing the raw material 1-naphthol (A-7) synthesized in Step 5 with tetrahydronaphthol. $^1$H NMR (400 MHZ, CD$_3$OH): 6.72 (s, 2H), 6.35 (d, J=8.0 Hz, 1H), 6.04 (d, J=8.0 Hz, 1H), 4.18 (d, J=12.0 Hz, 2H), 3.68 (s, 2H), 2.74 (t, J=4.0 Hz, 2H), 2.67 (t, J=12.0 Hz, 2H), 2.11 (s, 6H), 1.86 (m, J=64.0 Hz, 4H). MS m/z (ESI): 375.1 [M−1].

Embodiment 1: Preparation of ((4-((7-hydroxy-1,1-dimethyl-2,3-dihydro-1H-indene-4-position)methyl)-3,5-dimethylphenoxy) methyl) phosphoric acid (compound 1)

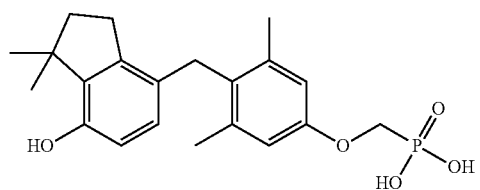

1

Using the synthetic route of reference embodiment A, compound 1 may be obtained by the following synthetic method.

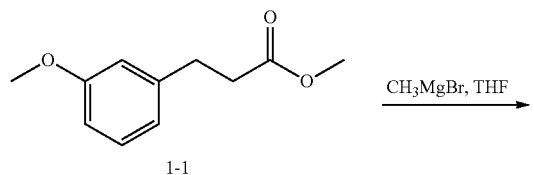

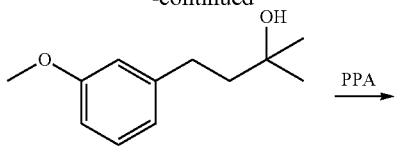

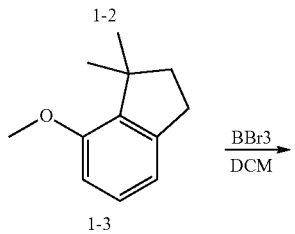

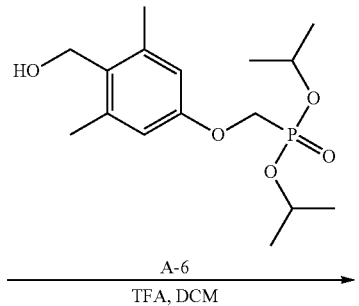

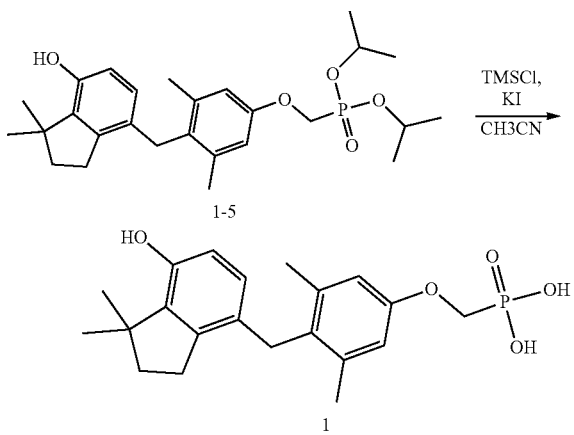

Step 1: Synthesis of compound 1-2

Compound 1-1 (1.94 g, 1.0 eq) was dissolved in 20 ml THF, the reaction system was replaced with nitrogen, then the temperature was lowered to around 0° C., 3M methylmagnesium bromide was slowly added dropwise, the temperature was kept below 5° C., addition dropwise was completed, and stirring was performed for 0.5 hours with the temperature kept. After the reaction was completed, a saturated ammonium chloride solution was added dropwise to the reaction solution to quench the reaction, extraction was performed with EA (50 ml*3), and the EA phase was washed with water (50 ml*2), washed with saturated brine (100 ml), dried with anhydrous sodium sulfate, and concentrated to obtain intermediate compound 1-2, 2.0 g.

$^1$H NMR (400 MHZ, CDCl): 7.26-7.17 (m, 1H), 6.81-6.72 (m, 2H), 3.79 (s, 3H), 2.70-2.66 (m, 2H), 1.81-1.77 (m, 2H), 1.28 (s, 6H).

Step 2: Synthesis of compound 1-3

Polyphosphoric acid (PPA) (2.9 g) was added to a reaction flask, then stirring was started, compound 1-2 (582 mg) was slowly added, and the reaction was stirred at room temperature for 2 hours. Ice water (100 ml) was added to quench the reaction, then extraction was performed with EA (100 ml*3), and the EA phases were combined, washed with water (50 ml*2) and saturated brine (100 ml), dried with anhydrous sodium sulfate, concentrated, and column-chromatographed to obtain compound intermediate compound 1-3, 50 mg.

$^1$H NMR (400 MHZ, CDCl$_3$): 7.14-7.10 (m, 1H), 6.80 (d, J=8.0 Hz, 1H), 6.69 (d, J=8.0 Hz, 1H), 3.82 (s, 3H), 2.89-2.85 (m, 2H), 1.91-1.88 (m, 2H), 1.36 (s, 6H).

Step 3: Synthesis of compound 1-4

Compound 1-3 (349 mg, 2 mmol) was dissolved in DCM (20 ml), the temperature was lowered to 0° C., and BBr3 (2 ml) was added dropwise. After the addition was completed, the reaction was stirred at 0° C. for 1 h. After the reaction, 10 ml of water was added, extraction was performed with EA to obtain the organic phase, and the organic phase was washed with 10 ml of brine, dried, concentrated, and column-chromatographed to obtain compound intermediate 1-4, 230 mg, which was directly put into the next reaction without purification.

Step 4: Synthesis of compound 1-5

Compound 1-4 (220 mg, 1.4 mmol) and A-6 (2.0 mmol) were dissolved in DCM (5 ml), the temperature was lowered to −1° C., TFA (307 µl, 4.1 mmol) was added dropwise, and the reaction was stirred for 1 h. After the completion of the reaction, 20 ml of DCM and 10 ml of water were added, extraction was performed with EA, the layers were separated to obtain an organic phase, and the organic phase was washed with 10 ml of water and 10 ml of brine, respectively. After drying, concentration and column chromatography (PE:EA=1:1), compound 1-5 (110 mg, pale yellow oily substance) was obtained. Step 5: Synthesis of compound 1:

Compound 1-5 (105 mg, 2.2 mmol), KI (118 mg, 0.71 mmol), and TMSCl (77 mg, 0.71 mmol) were dissolved in acetonitrile (1 ml), the temperature was raised to 50° C., and the reaction was stirred for 2 h. After the reaction, 10 ml of water and 10 ml of EA were added for extraction to obtain the organic phase, 10 ml of EA was again added to the aqueous phase for extraction, the organic phases were combined, dried, and concentrated, and preparation was performed with a thin-layer silica gel plate (DCM:MeOH=8:1) to obtain compound 1 (20 mg).

$^1$H NMR (400 MHZ, DMSO-d6): 6.71 (s, 2H), 6.32 (d, J=8.0 Hz, 1H), 6.09 (d, J=8.0 Hz, 1H), 4.03 (d, J=12.0 Hz, 2H), 3.73 (s, 2H), 2.88-2.85 (m, 2H), 1.94-1.91 (m, 2H), 1.37 (s, 6H). MS m/z (ESI): 389.1 [M−1].

Embodiment 2: Preparation of ((4-((7-hydroxy-1-methyl-2,3-dihydro-1H-indene-4-position) methyl)-3,5-dimethylphenoxy) methyl phosphoric acid (compound 2)

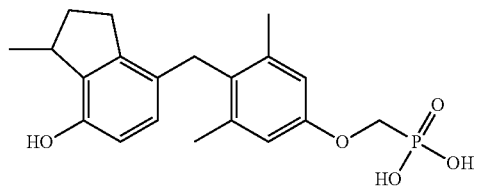

Using the route of synthesis of embodiment 1, compound 2 may be obtained by replacing the intermediate 1-4 synthesized in step 4 with 3-methyl-2,3-dihydro-1H-indene-4-ol.

MS m/z (ESI): 375.1 [M−1].

Embodiment 3: Preparation of ((4-((4-hydroxy-5,5-dimethyl-5,6,7,8-tetrahydronaphthalen-1-yl)methyl)-3,5-dimethylphenoxy) methyl) phosphoric acid (compound 3)

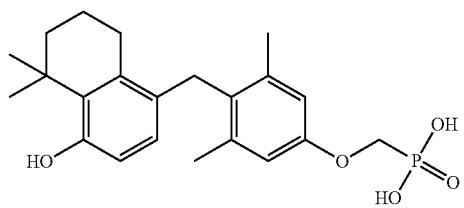

Compound 3 may be obtained using the route of synthesis of embodiment 1, wherein the synthesis of intermediate 3-4 is as follows.

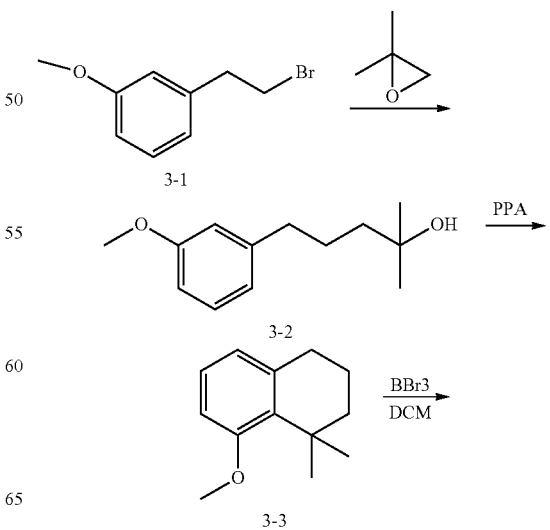

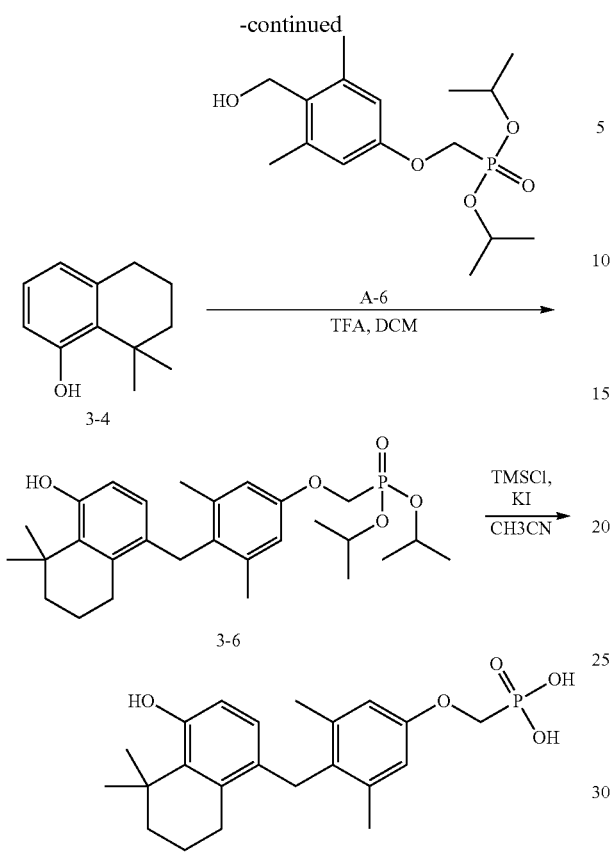

Step 1: Synthesis of compound 3-2

Mg powder (1.56 g, 65.1 mmol) was immersed in anhydrous ether (10 ml), and 1 pellet of I₂ was added. First, ⅓ of the raw material compound 3-1 (10 g, 46.5 mmol) was slowly added dropwise in an ether (10 ml) solution, then the remaining raw material compound 3-1 was slowly added dropwise after the reaction was induced, and microreflux was continued for 0.5 h. CuI (0.66 g, 3.5 mmol) and THF (10 ml) were added to another reaction flask, the temperature was lowered to −20° C., a prepared format reagent was added dropwise, dimethyl oxirane (5 ml, 55.8 mmol) was added dropwise after the addition was completed, and the reaction was stirred for 2 h. After the reaction, 20 ml of water was added to quench the reaction, and then 30 ml of EA was added to extract the organic phase, which was dried, concentrated, and column-chromatographed (PE: EA=10:1-1:1) to obtain intermediate compound 3-2 (4.2 g, a light yellow liquid).

Step 2: Synthesis of compound 3-3

Compound 3-1 (2.2 g, 10.6 mmol) was slowly added dropwise into PPA (10 g), the temperature was kept between 15-25° C., and, after the dropping was completed, the mixture was stirred at room temperature for 2 h. After the completion of the reaction, 10 ml of water and 10 ml of ether were added for extraction, and the aqueous phase was extracted 2 times with ether. The organic phases were combined, dried, concentrated, and subjected to column chromatography (PE) to obtain compound 3-3 (230 mg, a pale yellow oily substance).

Step 3: Synthesis of compound 3-3

Compound 3-2 (230 mg, 1.2 mmol) was dissolved in DCM (10 ml), the temperature was lowered to 0° C., BBr3 (1 ml) was added dropwise, and the reaction was stirred at 0° C. for 1 h. 10 ml of water was added to quench the reaction, and then 10 ml of DCM was added to extract the organic phase, which was dried, concentrated, and column-chromatographed (PE: EA=10:1) to obtain compound 3-4 (100 mg, a light yellow oily substance).

In steps 4 and 5, compound 3 may be prepared by using route of synthesis of embodiment 1.

¹H NMR (400 MHZ, DMSO-d6): 6.71 (s, 2H), 6.32 (d, J=8.0 Hz, 1H), 6.02 (d, J=12.0 Hz, 1H), 4.04 (d, J=12.0 Hz, 2H), 3.67 (s, 2H), 2.73-2.70 (m, 2H), 2.10 (s, 6H), 1.85-1.78 (m, 2H), 1.67-1.63 (m, 2H), 1.42 (s, 6H).

MS m/z (ESI): 403.1 [M−1].

Embodiment 4: Preparation of ((4-((4-hydroxy-5,5-dimethyl-6,7,8,9-tetrahydro-5H-benzo[7] annun-1-yl)methyl)-3,5-dimethylphenoxy) methyl) phosphoric acid (compound 4)

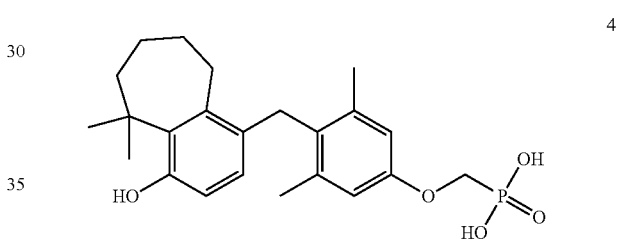

Using the route of synthesis of embodiment 1, compound 4 may be obtained, wherein the synthesis of intermediates 4-7 is as follows.

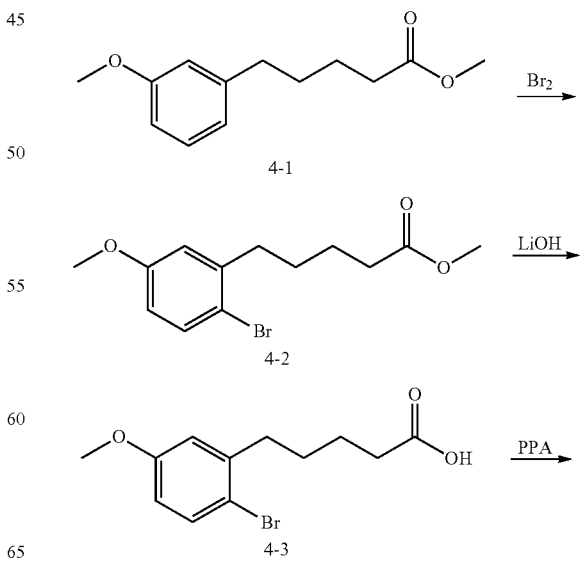

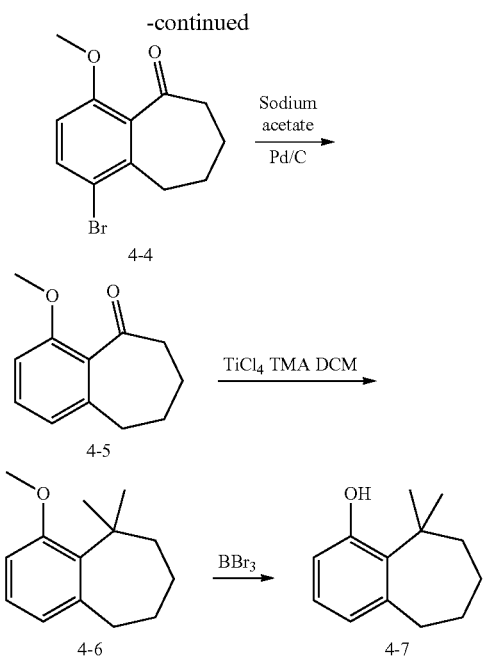

Step 1: Synthesis of compound 4-2

Compound 4-1 (4.4 g) was put into a reaction flask, chloroform (30 ml) was added, the temperature was lowered by stirring to 0° C., then liquid bromine (3.5 g/30 ml chloroform) was added dropwise, and, after the addition was completed, the reaction was stirred at room temperature for 0.5 h. The reaction was quenched with sodium sulfite solution (20 ml), and extraction with EA (100 ml*3), washing with water (50 ml*2), washing with saturated brine (50 ml), and drying with anhydrous sodium sulfate was performed to obtain a 5.3 g product.
$^1$H NMR (400 MHZ, CDCl$_3$): 7.40 (d, J=8.0 Hz, 1H), 6.76 (d, J=4.0 Hz, 1H), 6.63-6.60 (m, 1H), 3.77 (s, 3H), 3.67 (s, 3H), 2.71-2.67 (m, 2H), 2.38-2.34 (m, 2H), 1.74-1.63 (m, 4H).

Step 2: Synthesis of Compound 4-3

Compound 4-2 (5.7 g, 1.0 eq) was dissolved in THF (30 ml), water (30 ml) was added, lithium hydroxide monohydrate (3.9 g, 5.0 eq) was added with stirring, pH=2 was reached by adjustment with 4N hydrochloric acid after stirring overnight, and the mixture was extracted with EA (100 ml*3), washed with water (100 ml*2), washed with saturated brine (100 ml), dried with anhydrous sodium sulfate, and concentrated to obtain compound 4-3:5.3 g.

Step 3: Synthesis of Compound 4-4

Compound 4-3 (3.6 g) was added dropwise to PPA (240 g), the temperature was raised to 55° C., and the reaction was stirred for 4 h. Ice water (400 ml) was added to quench the reaction, and extraction with EA (150 ml*3), washing with water (100 ml*2), washing with saturated brine (100 ml), drying with anhydrous sodium sulfate, and concentration was performed to obtain oily compound 4-4:2.4 g. $^1$H NMR (400 MHZ, CDCl$_3$): 7.54 (d, J-8.0 Hz, 1H), 6.73 (d, J-8.0 Hz, 1H), 3.79 (s, 3H), 2.93-2.90 (m, 2H), 2.61-2.60 (m, 2H), 1.76 (m, 4H).

Step 4: Synthesis of Compound 4-5

Compound 4-4 (1.61 g, 1.0 eq) and sodium acetate (0.5 g, 1.0 eq) were put into a reaction flask, methanol (8 ml), dioxane (16 ml), and Pd/c (160 mg) were added, replacement with H$_2$ was performed, and the reaction was stirred overnight at room temperature under a hydrogen atmosphere. After filtration and concentration, the residue EA (200 ml) was dissolved, washed with water (50 ml*2), washed with saturated brine (50 ml), dried with anhydrous sodium sulfate, and concentrated to obtain yellow oily compound 4-5:1. 2 g.
$^1$H NMR (400 MHZ, CDCl): 7.29-7.25 (m, 1H), 6.83 (d, J=8.0 Hz, 1H), 6.74 (d, J=8.0 Hz, 1H), 3.81 (s, 3H), 2.75-2.72 (m, 2H), 2.65-2.63 (m, 2H), 1.82-1.80 (m, 4H).

Step 5: Synthesis of Compound 4-6

TiCl4 (7.8 g, 6.8 mmol) was dissolved in DCM (15 ml), the temperature was lowered to −50° C., (CH$_3$) 2Zn (41 ml, 0.1 M toluene solution) was added, stirring was performed for 0.5 h, 4-5 (1.3 g, dissolved in 40 ml DCM) was added dropwise, and the temperature was raised naturally with stirring overnight. After completion of the reaction, the reaction was quenched by adding 50 ml of water, the mixture was extracted 3 times with 50 ml of DCM, and the organic phases were combined, washed with 50 ml of brine, dried with anhydrous sodium sulfate, and concentrated. Column chromatography was performed to yield 4-6 (a 1 g colorless liquid).

Step 6: Synthesis of Compound 4-7

Compound 4-6 (1 g, 4.9 mmol) was dissolved in DCM (50 ml), the temperature was lowered to 0° C., BBr$_3$ (5 ml) was added, and the mixture was stirred at room temperature for 1 h. After the completion of the reaction, 50 ml of water was added to quench the reaction, and the DCM phase was extracted and washed with 50 ml of brine. It was dried with anhydrous sodium sulfate, concentrated, and column-chromatographed (PE: EA=100:1-10:1) to obtain compound 4-7 (335 mg, a colorless oily substance).
$^1$H NMR (400 MHZ, CD;OD): 6.80-6.76 (m, 1H), 6.56 (d, J=12.0 Hz, 1H), 6.48 (d, J=8.0 Hz, 1H), 2.84 (brs, 2H), 1.86-1.75 (m, 6H), 1.46 (s, 6H).

Compound 4 may be prepared by using intermediate 4-7 and following the route of synthesis of embodiment 1.
$^1$H NMR (400 MHZ,CD;OD): 9.29 (s, 1H), 6.63-6.21 (m, 2H), 6.38 (d, J=12.0 Hz, 1H), 6.12 (d, J=12.0 Hz, 1H), 4.42-4.32 (m, 1H), 3.76-3.69 (m, 4H), 2.61-2.55 (m, 2H), 2.05 (s, 6H), 1.65-1.53 (m, 6H), 1.11 (d, J=8.0 Hz, 6H).
MS m/z (ESI): 417.1 [M−1].

Embodiment 5: Preparation of ((4-((7-hydroxy-1,1-dimethyl-2,3-dihydro-1H-indene-4-position) oxy)-3,5-dimethylphenoxy) methyl) phosphoric acid (compound 5)

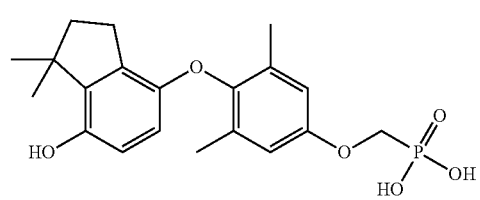

Using a route of synthesis similar to that in embodiment 1, compound 5 may be obtained. MS m/z (ESI): 391.1 [M−1].

Embodiment 6: Preparation of ((3,5-dichloro-4-((7-hydroxy-1,1-dimethyl-2,3-dihydro-1H-indene-4-position) methyl) phenoxy) methyl) phosphoric acid (compound 6)

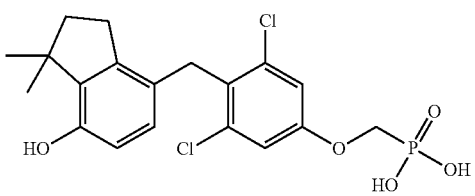

6

Using a route of synthesis similar to that in embodiment 1, compound 6 may be obtained. $^1$H NMR (400 MHZ, CD$_3$OD): 7.08 (s, 2H), 6.35 (d, J=8.4 Hz, 1H), 6.19 (d, J=8.4 Hz, 1H), 4.66-4.51 (m, 2H), 4.07-4.02 (m, 4H), 2.90 (t, J=14.7 Hz, 2H), 1.93 (t, J=14.7 Hz, 2H), 1.37 (m, 6H).
MS m/z (ESI): 429.5 [M−1].

Embodiment 7: Preparation of 4-(3-chlorophenyl)-2-((4-((7-hydroxy-1,1-dimethyl-2,3-dihydro-1H-indene-4-position) methyl)-3,5-dimethylphenoxy) methyl)-1,3,2-dioxaphosphorane 2-oxo (compound 7)

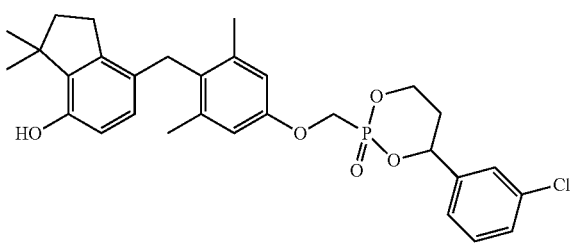

7

The following route of synthesis was used:

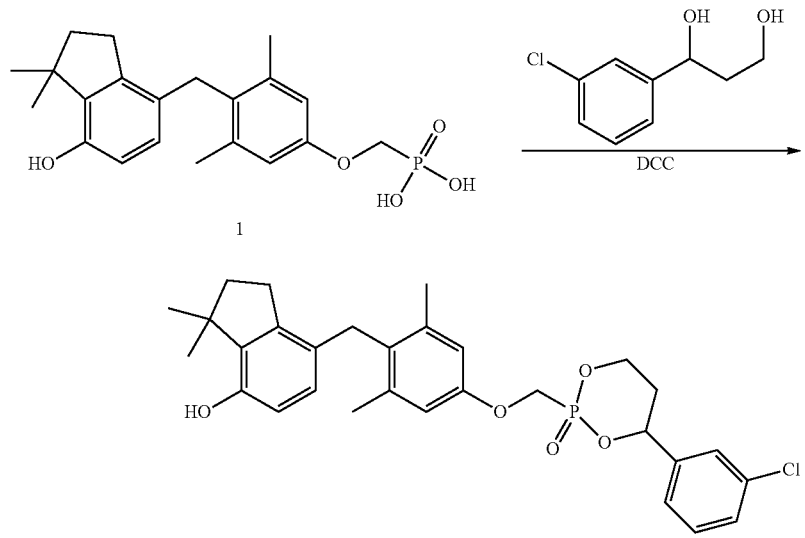

Compound 1 (211 mg, 0.54 mmol) and 1-(3-chlorophenyl) propane-1,3-diol (302 mg, 1.62 mmol) were dissolved in pyridine (1 ml) and DMF (5 ml), and DCC (334 mg, 1.62 mmol) was added at room temperature. The temperature was raised to 70° C. and stirring was performed for 4 h. After cooling to room temperature, the mixture was filtered, concentrated, and separated by column chromatography to obtain racemic compound 7 (100 mg).
MS m/z (ESI): 541.1 [M+1].

Embodiment 8: Preparation of (((((4-((7-hydroxy-1,1-dimethyl-2,3-dihydro-1H-indene-4-position) methyl)-3,5-dimethylphenoxy) methyl) phosphoryl) bis (oxy)) bis(methylene) bispivaloyl (compound 8)

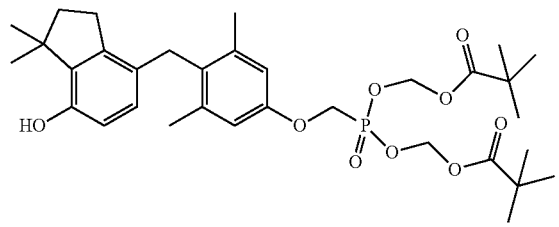

8

The following route of synthesis was used:

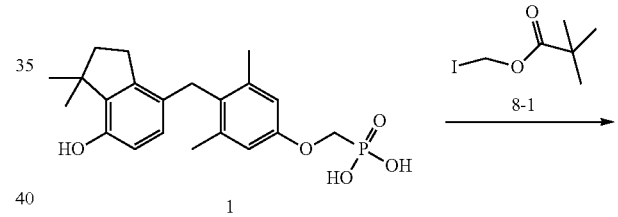

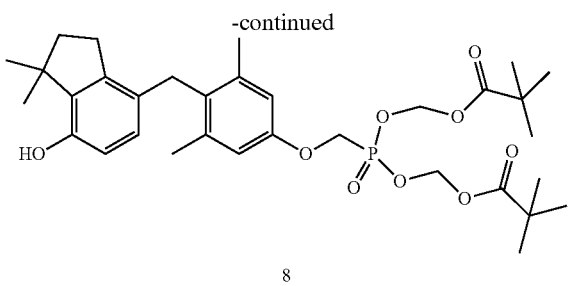

8

Diisopropylethylamine (140 mg, 1.08 mmol) was added to a solution of compound 1 (211 mg, 0.54 mmol) in acetonitrile (10 ml) at room temperature. The temperature was raised to 40° C., stirring was performed for half an hour, then iodide 8-1 (261 mg, 1.08 mmol) was added, and stirring was continued overnight. Then, addition of iodide 8-1 (261 mg, 1.08 mmol) and of diisopropylethylamine (140 mg, 1.08 mmol) was continued, and the reaction was continued at the temperature for 6 h. The reaction was quenched with 50 ml of water, and the EA phase was extracted and washed with 50 ml of brine. It was dried with anhydrous sodium sulfate, concentrated, and separated by column chromatography to obtain racemic compound 7 (150 mg).

MS m/z (ESI): 619.2 [M+1].

Embodiments 9 and 11: Preparation of compounds 9 and 11.

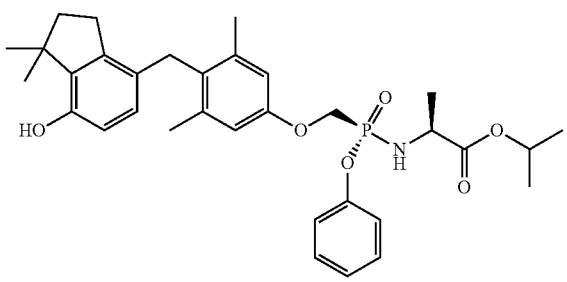

9

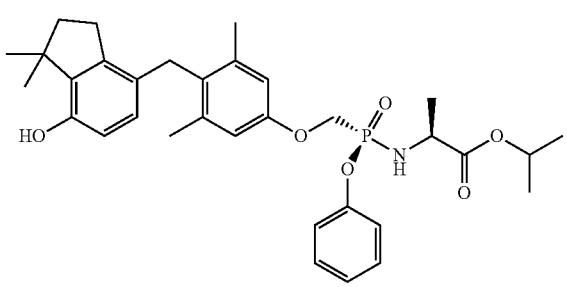

11

The following route of synthesis was used:

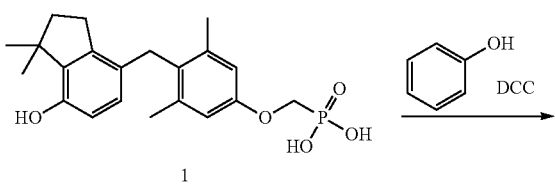

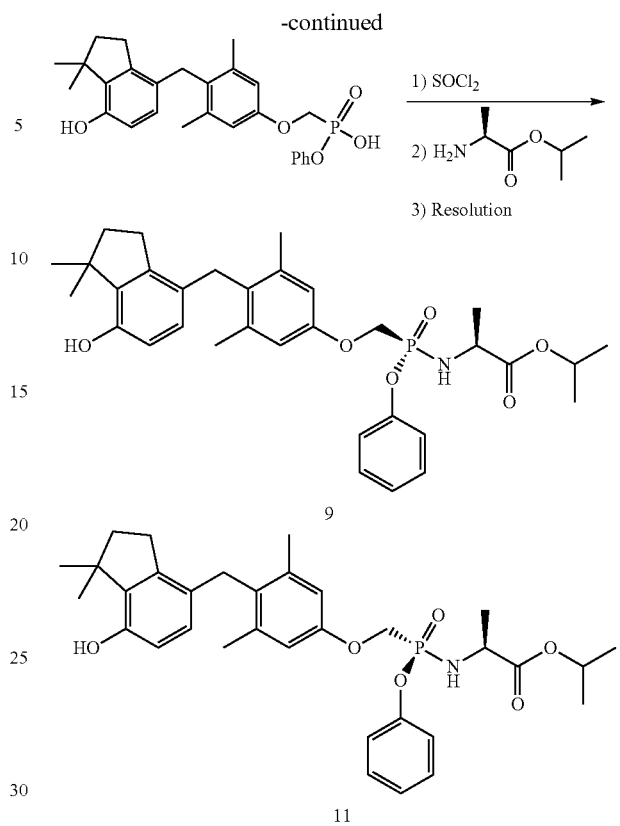

Step 1: Synthesis of intermediate 9-1

DMF (20 ml) and pyridine (4 ml) were added in turn to a mixture of compound 1 (780 mg, 2 mmol), phenol (376 mg, 4 mmol), DCC (1.24 g, 6 mmol), and DMAP (244 mg, 2 mmol), the temperature was raised to 80° C. after completion of the addition, and the reaction was stirred for 15 hours. After cooling, the solvent was directly concentrated under reduced pressure, and intermediate 9-1 (200 mg) was obtained by column chromatography.

MS m/z (ESI): 465.1 [M+1].

Step 2: Synthesis of compounds 9 and 11

Under an ice bath, thionyl chloride (1.72 mmol) was slowly added dropwise to a solution of compound 9-1 (200 mg, 0.43 mmol) and DMF (32 mg, 0.43 mmol) in dichloromethane (2 ml). After the dropwise addition was completed, the reaction system was heated to reflux and stirred for 3 h. The temperature was lowered to room temperature, L-alanine isopropyl ester hydrochloride (287 mg, 1.72 mmol) and diisopropylethylamine (222 mg, 1.72 mmol) were added to the reaction system, and the mixture was kept at room temperature and stirred for 15 hours. The reaction was quenched by adding water (50 ml), and extraction was performed 1 time with ethyl acetate (50 ml). The organic phase was concentrated under reduced pressure and resolved to obtain compounds 9 and 11.

Structure characterization of compound 9: MS m/z (ESI): 580.1 [M+1]. 1H NMR (400 MHZ,DMSO-d6): 8.79 (s, 1H), 7.38-7.34 (m, 2H), 7.23-7.15 (m, 3H), 6.70 (m, 2H), 6.35 (d, J=8.0 Hz, 1H), 6.01-5.99 (m, 1H), 5.90-5.84 (m, 1H), 4.78-4.70 (m, 1H), 4.32 (d, J=9.6 Hz, 2H), 4.00-3.93 (m, 1H), 3.66 (s, 2H), 2.84-2.80 (m, 2H), 2.09 (s, 6H), 1.87-1.83 (m, 2H), 1.30 (s, 6H), 1.19 (d, J=6.8 Hz, 3H), 1.10-1.08 (m, 6H).

Embodiment 10: Preparation of compound 10

Using a route of synthesis similar to that in embodiment 7, compound 10 may be obtained.

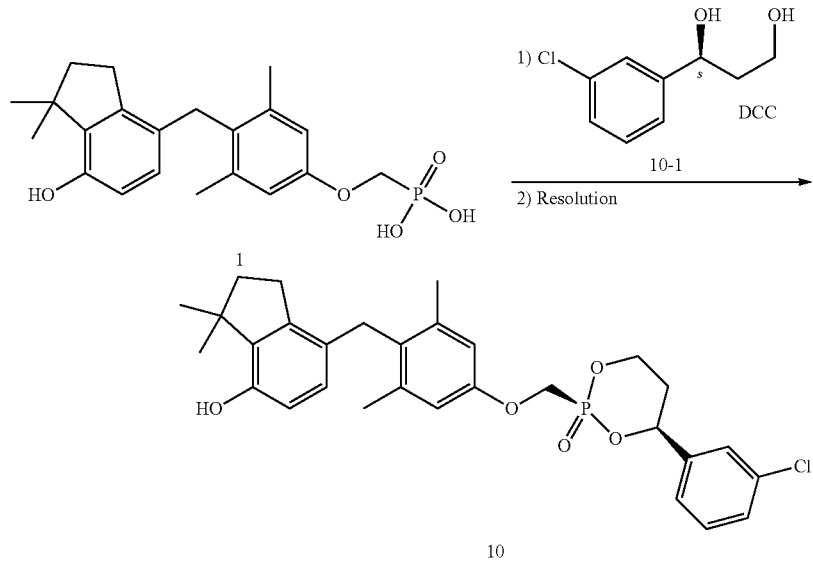

DMF (20 ml) and pyridine (4 ml) were added in turn to a mixture of compound 1 (780 mg, 2 mmol), compound 10-1 (1.16 g, 6 mmol) and DCC (1.24 g, 6 mmol). After the addition, the temperature was raised to 70° C. and stirring was performed for 18 hours. The solvent was concentrated under reduced pressure and resolved to obtain compound 10 (150 mg).
MS m/z (ESI): 541.1 [M+1].

$^1$H NMR (400 MHZ,DMSO-d6): 8.81 (s, 1H), 7.48 (s, 1H), 7.43-7.41 (m, 3H), 6.74 (s, 2H), 6.35 (d, J=7.6 Hz, 1H), 6.02 (d, J=7.6 Hz, 1H), 5.82 (m, 1H), 4.62-4.38 (m, 4H), 3.66 (s, 2H), 2.86-2.77 (m, 2H), 2.29-2.18 (m, 2H), 2.09 (s, 6H), 1.90-1.80 (m, 2H), 1.30 (s, 6H).

Using compound 2 as the starting material and following the routes of synthesis of embodiment 7-embodiment 11, the following compounds may be prepared.

| Embodiment | Structure | MS m/z(ESI) [M + 1] |
|---|---|---|
| 12 | *structure 12* | 526.9 |
| 13 | *structure 13* | 605.1 |

| Embodiment | Structure | MS m/z(ESI) [M + 1] |
|---|---|---|
| 14 | 14 | 566.1 |
| 15 | 15 | 526.9 |
| 16 | 16 | 566.1 |

Test embodiment 1: Test of the binding ability of the compound to TRα:

1. Main experimental materials and instruments:
Envision 2104 microplate reader
Biotin-SRC2-2 co-activating peptide purchased from Sangon Biotech (Shanghai) Co., Ltd.
TR-a LBD, GST purchased from Thermo Fisher (product No. PV4762)
Europium-conjugated anti-glutathione antibody purchased from Cisbio (product No. 61GSTKLB)
Streptavidin-D2 purchased from Cisbio (product No. 610SADAB)

2. Preparation and processing of compounds
2.1 Preparation of compound dimethyl sulfoxide stock solution
All compounds 1 to 6 were dissolved in dimethyl sulfoxide and prepared as a 10 millimole stock solution.
2.2 Storage of compounds
After being dissolved in dimethyl sulfoxide, compounds 1 to 6 may be stored in a desiccator at room temperature for three months. For long-term storage, they may be placed in a refrigerator at −20° C.

3. Experimental steps
3.1 Preparation of a 1× reaction buffer
3.2 Screening of compounds:
a) Positive drug triiodothyronine (T3) was diluted from 10 millimoles (100×) or the test compound from 1 millimole (100×) in a ratio of 1:3 in geometric proportion with 100% dimethyl sulfoxide to achieve a total of 10 concentrations.
b) 4× concentration gradient-diluted compounds were prepared with 1× reaction buffer.
c) 5 microliters of 4× concentration gradient-diluted compounds were added to a 384-well experiment plate.
d) 4×TRa LBD and 4×RXRa were prepared with 1× reaction buffer.
e) 5 microliters of 4× TRa LBD and 4×RXRa were added to a 384-well experiment plate.
f) 2×biotin-SRC2-2, 2×europium-conjugated anti-glutathione antibody and 2×streptavidin-d2 were prepared with 1× reaction buffer.
g) 10 microliters of 2×mixture (refer to step f) was added to a 384-well experiment plate.
h) The 384-well experiment plate was centrifuged in a centrifuge at 1000 rpm for 1 minute.

i) Incubation was carried out in the dark at room temperature for 1 hour.
j) The Envision 2104 microplate reader was used to record the fluorescence signal values at the wavelengths of 665 nm and 615 nm in each well of the 384-well experiment plate, and the fluorescence ratio of 665 nm/615 nm was calculated.

4. Data analysis 4.1 Calculation of the relative ratio of each hole (Ratio$_{665}$ nm/615 nm-RatioBlank)

4.2 The activity percentage was calculated as follows:

$$\text{Activity (\%)} = \frac{\overline{\text{Ratio}_{Compound}} - \overline{\text{Ratio}_{Blank}}}{\overline{\text{Ratio}_{Positive}} - \overline{\text{Ratio}_{Blank}}} \times 100$$

Ratio$_{Compound}$: Average of the relative ratios of the compound wells of the embodiments Ratio$_{Positive}$: Average of the relative ratios of all positive control wells.

Ratio$_{Blank}$: Average of the relative ratios of all negative control wells.

4.3 Drawing of curves and calculation of EC50:

EC50 was calculated by fitting the relationship between activity (%) and compound logarithmic concentration with Graphpad 5.0 by a nonlinear regression method.

Y=Bottom+ (top-bottom)/(1+10^((LogEC50−X)*slope))

X: Compound logarithmic concentration Y: Percentage activity

The specific test data are shown in Table 1 below.

Test embodiment 2: Test of the binding ability of the compound to TRB

1. Main experimental materials and instruments:

Envision 2104 microplate reader

Biotin-SRC2-2 co-activating peptide purchased from Sangon Biotech (Shanghai) Co., Ltd.

TRB LBD, GST purchased from Thermo Fisher (product No. PV4762)

Europium-conjugated anti-glutathione antibody purchased from Cisbio (product No. 61GSTKLB)

Streptavidin-D2 purchased from Cisbio (product No. 610SADAB)

2. Preparation and processing of compounds 2.1 Preparation of compound dimethyl sulfoxide stock solution All compounds 1 to 6 were dissolved in dimethyl sulfoxide and prepared as a 10 millimole stock solution.

2.2 Storage of compounds

After being dissolved in dimethyl sulfoxide, the compounds may be stored in a desiccator at room temperature for three months. For long-term storage, they may be placed in a refrigerator at −20° C.

3. Experimental steps 3.1 Preparation of a 1× reaction buffer 3.2 Screening of compounds:

a) Positive drug triiodothyronine (T3) was diluted from 10 micromoles (100×) or the test compound from 1 millimole (100×) in a ratio of 1:3 in geometric proportion with 100% dimethyl sulfoxide to achieve a total of 10 concentrations.

b) 4× concentration gradient-diluted compounds were prepared with 1× reaction buffer.

c) 5 microliters of 4× concentration gradient-diluted compounds were added to a 384-well experiment plate.

d) 4×TRB LBD and 4×RXRB were prepared with 1× reaction buffer.

e) Add 5 microliters of 4× TRB LBD and 4×RXRB to a 384-well experiment plate.

f) 2×biotin-SRC2-2, 2×europium-conjugated anti-glutathione antibody and 2×streptavidin-d2 were prepared with 1× reaction buffer.

g) 10 microliters of 2×mixture (refer to step f) was added to a 384-well experiment plate.

h) The 384-well experiment plate was centrifuged in a centrifuge at 1000 rpm for 1 minute.

i) Incubation was carried out in the dark at room temperature for 1 hour.

j) The Envision 2104 microplate reader was used to record the fluorescence signal values at 665 nm and 615 nm in each well of the 384-well experiment plate, and the ratio 665 nm/615 nm was calculated.

4. Data analysis 4.1 Calculation of the relative ratio of each hole (Ratio$_{665}$ nm/615 nm-Ratio$_{Blank}$)

4.2 The activity percentage was calculated as follows:

$$\text{Activity (\%)} = \frac{\overline{\text{Ratio}_{Compound}} - \overline{\text{Ratio}_{Blank}}}{\overline{\text{Ratio}_{Positive}} - \overline{\text{Ratio}_{Blank}}} \times 100$$

Ratio$_{Compound}$: Average of the relative ratios of the compound wells of the embodiments Ratio$_{Positive}$: Average of the relative ratios of all positive control wells.

Ratio$_{Blank}$: Average of the relative ratios of all negative control wells.

4.3 Drawing of curves and calculation of EC50:

EC50 was calculated by fitting the relationship between activity (%) and compound logarithmic concentration with Graphpad 5.0 by a nonlinear regression method.

Y=Bottom+ (top-bottom)/(1+10^((LogEC50−X)*slope))

X: Compound logarithmic concentration Y: Percentage activity

The specific test data are shown in Table 1 below. The selectivity algorithm was calculated after being standardized with T3 on the basis of the literature (A Pharmacology Primer Techniques for More Effective and Strategic Drug Discovery, 4th Edition, Page 220).

TABLE 1

Binding activities of the compounds to thyroxine receptor β:

| Com- pound | THR-β | | THR-α | | α/β selectivity (multiple) |
|---|---|---|---|---|---|
| | EC$_{50}$(uM) | Emax(%) | EC$_{50}$(uM) | Emax(%) | |
| Reference compound A | 0.109 | 100.00 | 0.280 | 106.50 | 4.7 |
| Reference compound B | 0.041 | 110.70 | 0.23 | 105.70 | 11.4 |
| 1 | 0.012 | 104.10 | 0.041 | 96.42 | 7.0 |
| 2 | <0.100 | 103.60 | <0.200 | 98.30 | — |
| 3 | 0.104 | 100.00 | 0.270 | 104.80 | 4.8 |
| 4 | >1 | | >10 | | — |
| 5 | <0.100 | 109.50 | <0.200 | 102.10 | — |
| 6 | 0.108 | 79.04 | 0.05 | 99.15 | 0.7 |
| MB07444 | 0.033 | 113.00 | 0.051 | 112.60 | 2.9 |
| T3 | 0.0004 | 98.31 | 0.0002 | 106.70 | 1.0 |

Conclusion: Compared with the published comparative compound MB07444, most compounds of the present invention unexpectedly showed very high selectivity; in addition, the activity of compound 1 for THR-β was much higher than that of the contrast compound MB07444. Even compared with the naphthol reference compound A, a compound of the present invention still had higher activity and selectivity.

Test 3: Drug metabolism experiment on prodrug in SD rats

In the experiment, two groups of 12 male SD rats having similar body weights were selected and orally administered compound 9, compound 10, and the control drug VK2809 (the prodrug of MB07444, structured as shown below) at a dose of 3 mg/kg at a single time, respectively, and blood and liver samples were collected at different time points.

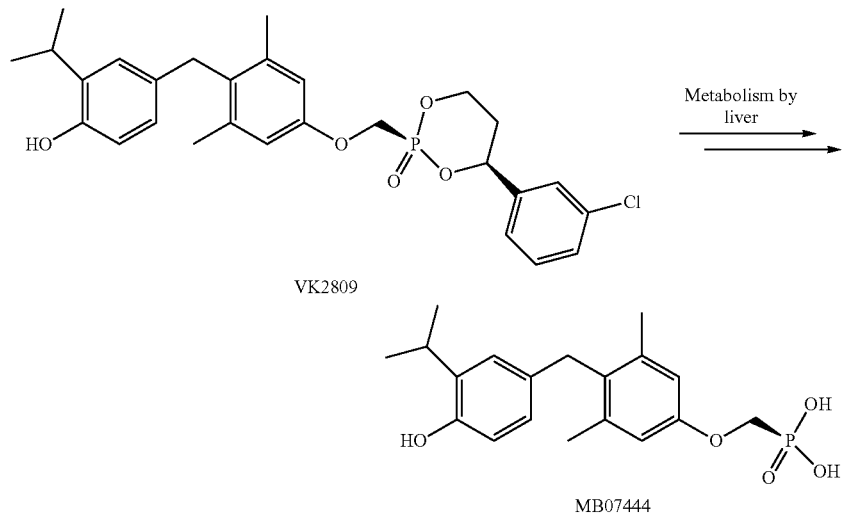

Preparation of Test Products

Solutions of compound 9/compound 10 and VK2809 with a final concentration of 0.6 mg/mL were respectively prepared, and the ratio between the solvents used for the preparation was PEG400: pure water =50:50 (v/v).

Group and Dose

No randomization was performed. The weights of the animals were measured before administration, and healthy animals with similar body weights were selected for inclusion in the experiment. The oral dose was 3 mg/kg.

Sample Collection

At least 0.2 mL of blood was collected from the tail vein or jugular vein, and heparin sodium was used as the anticoagulant.

Acquisition Time 15 min, 30 min, 1 h, 2 h, 4 h, 6 h, 8 h, 24 h after administration.

Sample Treatment

After being collected, a blood sample was placed in a marked ice-water bath centrifuge tube, plasma was quickly separated by centrifugation under centrifugation conditions: 3500 rpm, 10 minutes, and 4° C., and the plasma was stored under −40° C. for testing.

After the liver sample was collected, its surface was washed with normal saline, dried with medical gauze, placed in a labeled small ziplock bag, and stored under −40° C. for testing.

Sample Analysis

Liquid Chromatography-Mass Spectrography Conditions
  Liquid chromatography conditions:
  HPLC: LC-20ADxR, SHIMADZU
  Liquid phase pump: LC-20ADXR
  Column thermostat: CTO-20A
  Autosampler: SIL-20ACXR
  Controller: CBM-20A
  Degasser: DUG-20A3R chromatographic column: ZORBAX Eclipse Plus C18 2.1*50 mm, 3.5 μm, Agilent
  Precolumn: Guard column C18 4*2.0 mm, Phenomenex
  Mobile phase: A: 2 mM ammonium acetate aqueous solution;
  B: Acetonitrile;
  Autosampler needle washing liquid: 80% acetonitrile aqueous solution
  Autosampler needle washing program: washing mode: before and after suction
  Flushing volume: 200 μL
  Flushing speed: 35 L/sec
  Mobile phase gradient:

| Time (min) | A % | B % |
|---|---|---|
| 0.01 | 75 | 25 |
| 0.50 | 10 | 90 |
| 1.85 | 10 | 90 |
| 1.90 | 75 | 25 |
| 2.50 | | Stop |

Flow rate: 0.75 mL/min
Autosampler temperature: 4° C.
Injection volume: 2 μL
Running time: 2.50 min
Mass spectrometry analysis conditions:

Q TRAP6500 mass spectrometer with ESI source was used to perform negative ion MRM scanning. An LC-MS/MS analysis method was used to detect the contents of compound 9, compound 10 and its active metabolite 1, VK2809 and its active metabolite MB07444 in the plasma and liver. The metabolic kinetics data analysis software WinNonlin 7.0 was used to calculate the concentration data of plasma, and the non-compartmental model (NCA) method was used to calculate the pharmacokinetic parameters.

Results and Analysis:

The main pharmacokinetic parameters of the plasma of the SD rats are listed in Table 2 below:

TABLE 2

| Administration | Compound | Kel (1/h) | $T_{max}$ (h) | $C_{max}$ (ng/mL) | $AUC_{0-t}$ (ng·h/mL) | $AUC_{0-\infty}$ (ng·h/mL) | $t_{1/2}$ (h) |
|---|---|---|---|---|---|---|---|
| Compound 9 | Compound 9 | — | — | BLQ | BLQ | BLQ | — |
|  | Compound 1 | 0.147 | 4.67 | 134 | 1287 | 1347 | 4.82 |
| Compound 10 | Compound 10 | 0.428 | 4.67 | 19.9 | 69.2 | 89.3 | 1.73 |
|  | Compound 1 | 0.154 | 6.67 | 45.1 | 586 | 613 | 4.59 |
| VK2809 | VK2809 | 0.273 | 6.00 | 9.9 | 43.6 | 83.3 | 4.81 |
|  | MB07444 | 0.131 | 7.33 | 38.8 | 420 | 448 | 5.29 |

Conclusion: After being orally administered to the rats, the prodrug compounds 9 and 10, like the control drug VK2809, were quickly transformed into the active parent drug compound 1. In addition, the concentrations of both in plasma were not high.

The parameters of concentration in the livers of the SD rats and a comparison with the concentration in plasma are shown in Table 3 below:

TABLE 3

| Administration 3 mg/kg | Test drug |  | Ct(ng/g) |  |  |  |
|---|---|---|---|---|---|---|
|  |  |  | 1 h | 4 h | 8 h | 24 h |
| Compound 9 | Compound 9 (prodrug) | Blood | BLQ | BLQ | BLQ | BLQ |
|  |  | Liver | BLQ | BLQ | BLQ | BLQ |
|  |  | Liver-to-blood ratio | — | — | — | — |
|  | Compound 1 (parent drug) | Blood | 15.0 | 96.3 | 29.9 | 8.4 |
|  |  | Liver | 312 | 1563 | 762 | 396 |
|  |  | Liver-to-blood ratio | 20.8 | 16.2 | 25.5 | 47.1 |
| Compound 10 | Compound 10 (prodrug) | Blood | 8.8 | 7.9 | 10.3 | BLQ |
|  |  | Liver | 141 | 273 | 46.5 | BLQ |
|  |  | Liver-to-blood ratio | 16.2 | 7.8 | 4.7 | — |
|  | Compound 1 (parent drug) | Blood | 5.4 | 28.4 | 43.6 | 3.83 |
|  |  | Liver | 693 | 2578 | 1710 | 431 |
|  |  | Liver-to-blood. ratio | 29.1 | 20.6 | 17.7 | 121 |
| VK-2809 | VK-2809 (prodrug) | Blood | 2.9 | 4.8 | 5.6 | BLQ |
|  |  | Liver | 39 | 30 | 17 | BLQ |
|  |  | Liver-to-blood ratio | 8.6 | 5.2 | 4.0 | — |
|  | MB07444 (parent drug) | Blood | 5.9 | 16.9 | 29.6 | 3.6 |
|  |  | Liver | 214 | 952 | 542 | 37 |
|  |  | Liver-to-blood ratio | 15.9 | 14.0 | 13.6 | 9.9 |

Conclusion: The ability of the prodrug compound 10 prepared according to the present invention to transform into active metabolite drug 1 in the liver was much better than that of VK2809. Under the same prodrug dose, the absolute concentration of active metabolite compound 1 in the liver was at least three times that of the active metabolite drug MB07444 of the control drug VK2809, and its liver-to-blood ratio was also significantly higher than that of the control drug. Similarly, prodrug compound 9 may also be rapidly metabolized in the liver to produce active metabolite compound 1, and its absolute concentration is also higher than that of the control drug VK2809. The above data show that compounds of the present invention and prodrugs thereof are drugs with better liver-targeting properties, and have unparalleled pharmaceutical quality.

The above-described embodiments are intended only to explain the technical ideas and characteristics of the present invention, serving the purpose of enabling those of ordinary skill in the art to understand the contents of the present invention and implement the present invention, instead of limiting the scope of the present invention. Modifications or alterations made to the above-mentioned embodiments without departing from the spirit of the present invention shall fall within the scope of the present invention.

The invention claimed is:

1. A compound shown in formula (I) or a stereoisomer thereof or a pharmaceutically acceptable salt thereof,

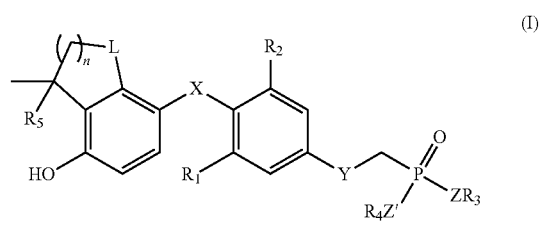

wherein
R$_1$ and R$_2$ are each independently selected from a halogen atom or a $C_{1-6}$ alkyl group;
R$_3$ and R$_4$ are each independently selected from hydrogen, a $C_{1-6}$ alkyl group, an unsubstituted phenyl group, a phenyl group substituted with at least one substituent selected from a halogen atom, a trifluoromethyl group, a $C_{1-6}$ alkyl group, a $C_{1-6}$ alkoxyl group or a cyano group, an unsubstituted naphthyl group, a naphthyl group substituted with at least one substituent selected from a halogen atom, a trifluoromethyl group, a $C_{1-6}$ alkyl group, a $C_{1-6}$ alkoxyl group or a cyano group,

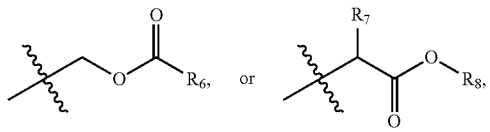

or $R_3$, $R_4$, and adjacent

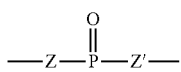

jointly form the following six-membered ring

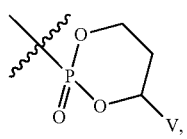

wherein V is an unsubstituted five-to ten-membered aryl group, a five-to ten-membered aryl group substituted with at least one substituent selected from a halogen atom, a trifluoromethyl group, a $C_{1-6}$ alkyl group, a $C_{1-6}$ alkoxyl group or a cyano group, an unsubstituted five-to ten-membered heteroaryl group containing 1 or 2 heteroatoms selected from N, S and O, or a five-to ten-membered heteroaryl group that is substituted with at least one substituent selected from a halogen atom, a trifluoromethyl group, a $C_{1-6}$ alkyl group, a $C_{1-6}$ alkoxyl group or a cyano group and that contains one or two heteroatoms selected from N, S or O;

$R_5$ is selected from H or a $C_{1-6}$ alkyl group;
$R_6$, $R_7$, and $R_8$ are each independently a $C_{1-6}$ alkyl group;
X is selected from —O— or —CH$_2$—;
Y is selected from —O— or —CH$_2$—;
Z and Z' are each independently selected from —O— or —NH—;
L is selected from —O—, —S— or —CH$_2$—; and
n is 1, 2 or 3;
wherein the halogen atom is selected from F, Cl or Br.

2. The compound or a stereoisomer thereof or a pharmaceutically acceptable salt thereof as claimed in claim 1, characterized in that $R_1$ and $R_2$ are each independently selected from F, Cl, Br, or —CH$_3$.

3. The compound or a stereoisomer thereof or a pharmaceutically acceptable salt thereof as claimed in claim 2, characterized in that $R_1$ and $R_2$ are both Cl.

4. The compound or a stereoisomer thereof or a pharmaceutically acceptable salt thereof as claimed in claim 2, characterized in that $R_1$ and $R_2$ are both -CH$_3$.

5. The compound or a stereoisomer thereof or a pharmaceutically acceptable salt thereof as claimed in claim 1, characterized in that $R_5$ is selected from H or —CH$_3$.

6. The compound or a stereoisomer thereof or a pharmaceutically acceptable salt thereof as claimed in claim 1, characterized in that n is 1 or 2.

7. The compound or a stereoisomer thereof or a pharmaceutically acceptable salt thereof as claimed in claim 6, characterized in that n is 1.

8. The compound or a pharmaceutically acceptable salt or a stereoisomer thereof as claimed in claim 1, characterized in that X is —CH$_2$—.

9. The compound or a stereoisomer thereof or a pharmaceutically acceptable salt thereof as claimed in claim 1, characterized in that Y is —O—.

10. The compound or a stereoisomer thereof or a pharmaceutically acceptable salt thereof as claimed in claim 1, characterized in that V is an unsubstituted phenyl group, a phenyl group substituted with at least one substituent selected from a halogen atom, a trifluoromethyl group, a $C_{1-3}$ alkyl group or a $C_{1-3}$ alkoxyl group, an unsubstituted five-to six-membered monocyclic heteroaryl group containing 1 or 2 heteroatoms selected from N, S or O, or a five-to six-membered monocyclic heteroaryl group that is substituted with at least one substituent selected from a halogen atom, a trifluoromethyl group, a $C_{1-3}$ alkyl group or a $C_{1-3}$ alkoxyl group and that contains 1 or 2 heteroatoms selected from N, S, or O.

11. The compound or a stereoisomer thereof or a pharmaceutically acceptable salt thereof as claimed in claim 1, characterized in that the compound has the structure shown in the formula (II) below:

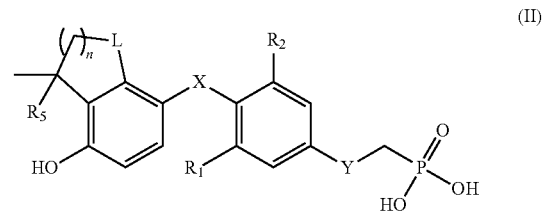

wherein
$R_1$, $R_2$, $R_5$, X, Y, L, and n are as defined in claim 1.

12. The compound or a stereoisomer thereof or a pharmaceutically acceptable salt thereof as claimed in claim 11, characterized in that
$R_1$ and $R_2$ are both —CH$_3$;
$R_5$ is —CH$_3$;
X is —CH$_2$—;
Y is —O—;
L is —CH$_2$—; and
n is 1 or 2.

13. The compound or a stereoisomer thereof or a pharmaceutically acceptable salt thereof as claimed in claim 1, characterized in that the compound has the structure shown in formula (III) below:

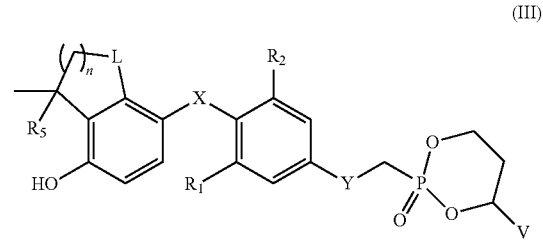

wherein
$R_1$, $R_2$, $R_5$, X, Y, L, n, and V are as defined in claim 1.

14. The compound or a stereoisomer thereof or a pharmaceutically acceptable salt thereof as claimed in claim 13, characterized in that $R_1$ and $R_2$ are both —$CH_3$;
$R_5$ is —$CH_3$;
X is —$CH_2$—;
Y is —O—;
L is —$CH_2$—;
n is 1 or 2; and
V is an unsubstituted phenyl group, a phenyl group substituted with at least one substituent selected from a halogen atom, a trifluoromethyl group, a $C_{1-3}$ alkyl group or a $C_{1-3}$ alkoxyl group, a pyridyl group, or a pyridyl group substituted with at least one substituent selected from a halogen atom, a trifluoromethyl group, a $C_{1-3}$ alkyl group, or a $C_{1-3}$ alkoxyl group.

15. The compound or a stereoisomer thereof or a pharmaceutically acceptable salt thereof as claimed in claim 14, characterized in that V is an m-chlorophenyl group.

16. The compound or a stereoisomer thereof or a pharmaceutically acceptable salt thereof as claimed in claim 1, characterized in that the compound has the structure shown in formula (IV) below:

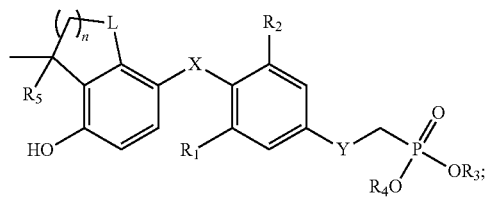

wherein
$R_1$, $R_2$, $R_5$, X, Y, L, and n are as defined in claim 1; and
$R_3$ and $R_4$ are each independently selected from a $C_{1-6}$ alkyl group, a phenyl group, a phenyl group substituted with at least one substituent selected from a halogen atom, a trifluoromethyl group, a $C_{1-6}$ alkyl group, a $C_{1-6}$ alkoxyl group or a cyano group, a naphthyl group, or a naphthyl group substituted with at least one substituent selected from a halogen atom, a trifluoromethyl group, a $C_{1-6}$ alkyl group, a $C_{1-6}$ alkoxyl group or a cyano group, or

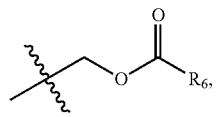

wherein $R_6$ is a $C_{1-6}$ alkyl group.

17. The compound or a stereoisomer thereof or a pharmaceutically acceptable salt thereof as claimed in claim 16, characterized in that $R_1$ and $R_2$ are both —$CH_3$;
$R_5$ is —$CH_3$;
X is —$CH_2$—;
Y is —O—;
L is —$CH_2$—;
n is 1 or 2; and
$R_3$ and $R_4$ are both

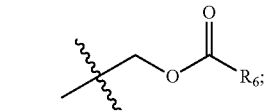

wherein $R_6$ is a $C_{1-6}$ alkyl group.

18. The compound or a stereoisomer thereof or a pharmaceutically acceptable salt thereof as claimed in claim 17, characterized in that $R_3$ and $R_4$ are both

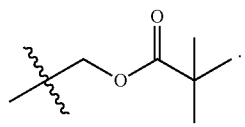 [SMILES: *COC(=O)C(C)(C)C]

19. The compound or a stereoisomer thereof or a pharmaceutically acceptable salt thereof as claimed in claim 1, characterized in that the compound has the structure shown in formula (V) below:

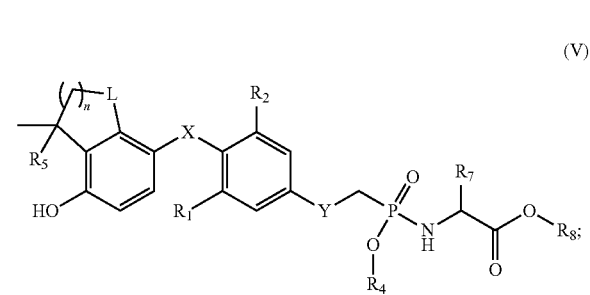

wherein
$R_1$, $R_2$, $R_5$, X, Y, L, and n are as defined in claim 1;
$R_4$ is selected from a $C_{1-6}$ alkyl group, a phenyl group, a phenyl group substituted with at least one substituent selected from a halogen atom, a trifluoromethyl group, a $C_{1-6}$ alkyl group, a $C_{1-6}$ alkoxyl group or a cyano group, a naphthyl group, or a naphthyl group substituted with at least one substituent selected from a halogen atom, a trifluoromethyl group, a $C_{1-6}$ alkyl group, a $C_{1-6}$ alkoxyl group or a cyano group, and $R_7$ and $R_5$ are each independently a $C_{1-6}$ alkyl group.

20. The compound or a stereoisomer thereof or a pharmaceutically acceptable salt thereof as claimed in claim 19, characterized in that $R_1$ and $R_2$ are both —$CH_3$;
$R_5$ is —$CH_3$;
X is —$CH_2$—;
Y is —O—;
L is —$CH_2$—;
n is 1 or 2;
$R_4$ is a phenyl group or a naphthyl group;
$R_7$ is a methyl group; and
$R_8$ is an ethyl group or an isopropyl group.

21. The compound or a stereoisomer thereof or a pharmaceutically acceptable salt thereof as claimed in claim 1, characterized in that the compound or a pharmaceutically acceptable salt or isomer thereof is selected from the group consisting of:

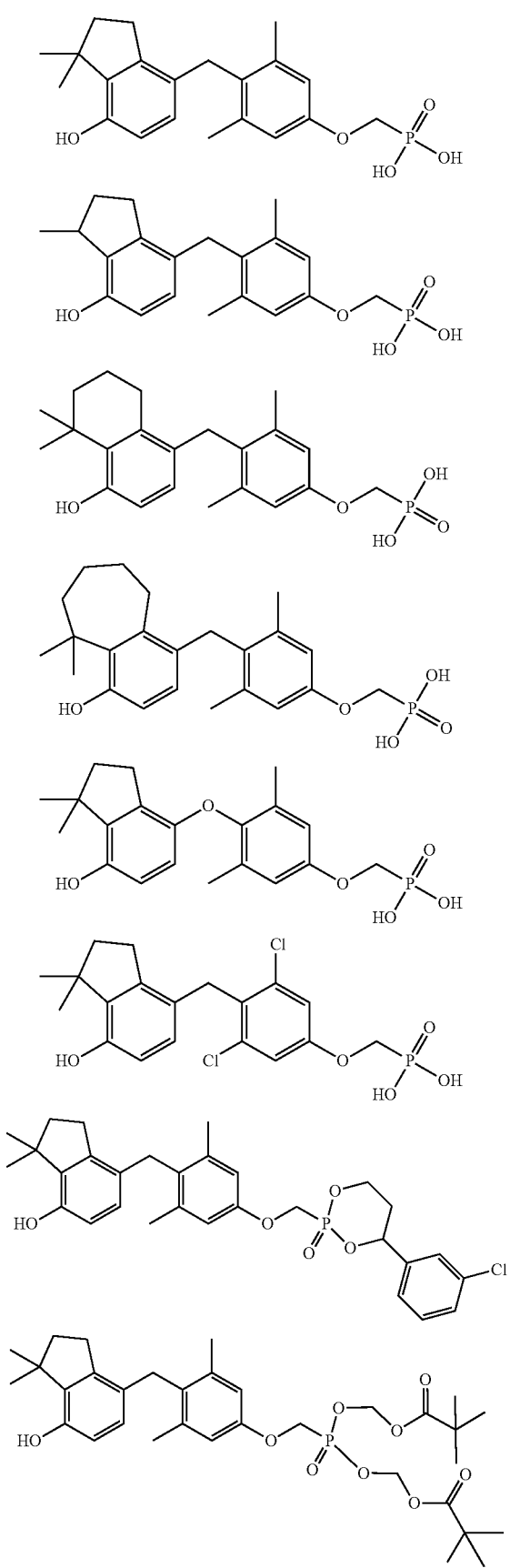
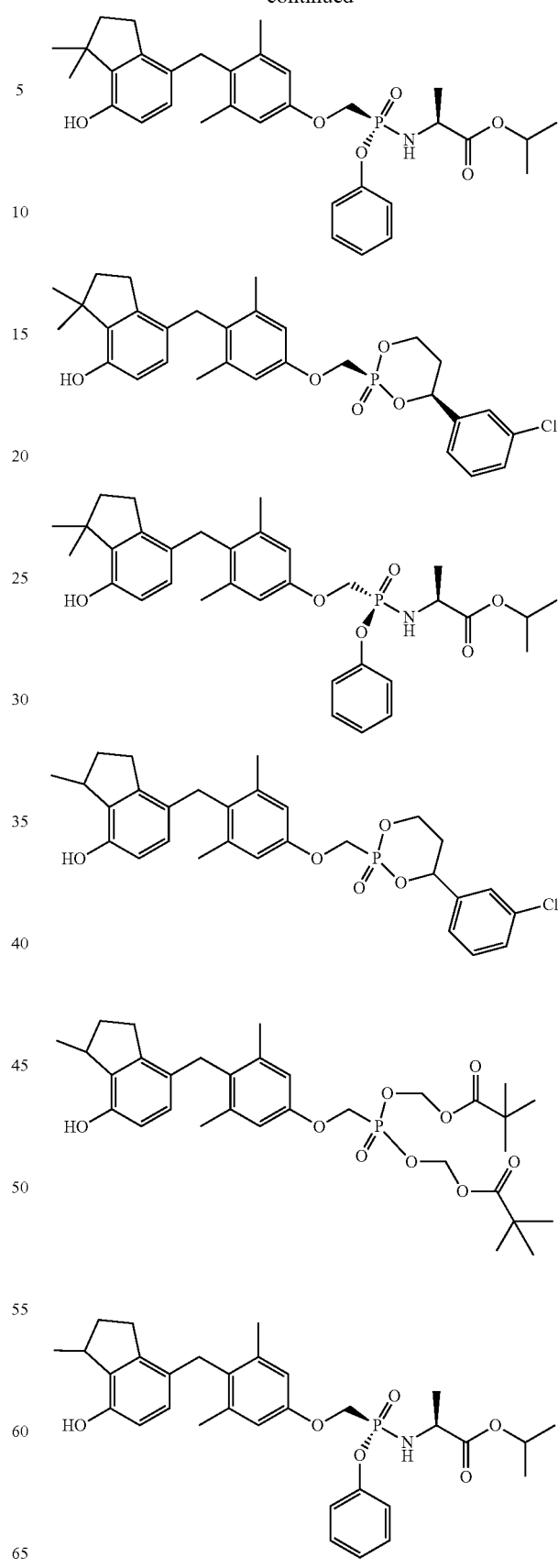

-continued

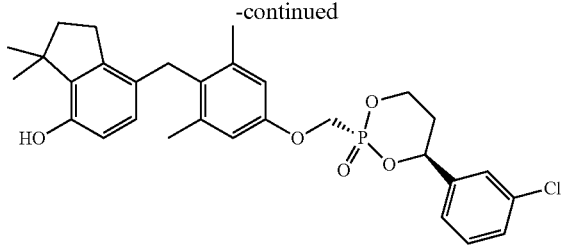

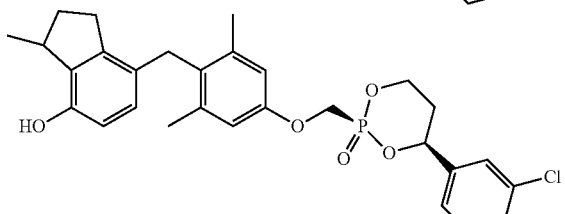

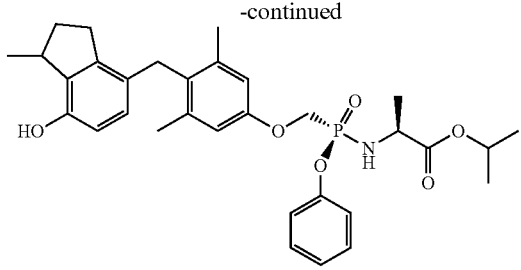

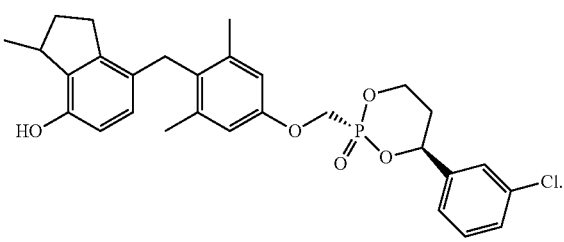

and

22. A pharmaceutical composition comprising a therapeutically effective amount of the compound or a stereoisomer thereof or a pharmaceutically acceptable salt thereof as claimed in claim 1 and a pharmaceutically acceptable excipient.

23. A method for treating a metabolism-related disease or fibrosis —related disease, wherein the metabolism-related disease or fibrosis —related disease is selected from: obesity, hyperlipidemia, hypercholesterolemia, diabetes, non-alcoholic steatohepatitis (NASH), hepatic steatosis, atherosclerosis, hypothyroidism, thyroid cancer, liver fibrosis, or pulmonary fibrosis, the method comprising administering to a subject an effective amount of the compound according to claim 1 or a pharmaceutical composition comprising the compound and a stereoisomer thereof or a pharmaceutically acceptable salt thereof as active ingredients.

24. The method for treating a metabolism-related disease as claimed in claim 23, wherein the metabolism-related disease is selected from: non-alcoholic steatohepatitis (NASH), hypothyroidism, thyroid cancer, liver fibrosis, or pulmonary fibrosis.

* * * * *